US008389262B2

(12) United States Patent
Minning et al.

(10) Patent No.: US 8,389,262 B2

(45) Date of Patent: Mar. 5, 2013

(54) SUBTILASE VARIANTS HAVING ALTERED IMMUNOGENICITY

(75) Inventors: Stefan Minning, Frederiksberg C (DK); Henriette Draborg, Allerod (DK); Erwing Ludo Roggen, Lyngby (DK); Nanna Kristensen Soni, Copenhagen (DK); Ninna Willestofte Berg, Ballerup (DK); Stina Thulesen Lyngstrand, Roskilde (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/888,854

(22) Filed: Sep. 23, 2010

(65) Prior Publication Data

US 2011/0009308 A1 Jan. 13, 2011

Related U.S. Application Data

(63) Continuation of application No. 11/547,555, filed as application No. PCT/DK2005/000225 on Apr. 1, 2005, now Pat. No. 7,824,896.

(60) Provisional application No. 60/564,131, filed on Apr. 21, 2004.

(30) Foreign Application Priority Data

Apr. 2, 2004 (DK) ................................ 2004 00535

(51) Int. Cl.

*C12N 9/54* (2006.01)
*C12N 15/57* (2006.01)
*C12N 15/74* (2006.01)
*C11D 3/386* (2006.01)
*C12N 15/75* (2006.01)
*C12P 21/00* (2006.01)

(52) U.S. Cl. .................... 435/221; 435/69.1; 435/252.3; 435/252.31; 435/320.1; 510/300

(58) Field of Classification Search ........................ None
See application file for complete search history.

(56) References Cited

U.S. PATENT DOCUMENTS

| | | | | |
|---|---|---|---|---|
| 5,665,587 | A * | 9/1997 | Aaslyng et al. | 435/221 |
| 5,741,694 | A * | 4/1998 | Hastrup et al. | 435/222 |
| 5,837,517 | A * | 11/1998 | Sierkstra et al. | 435/221 |
| 5,858,757 | A * | 1/1999 | Von Der Osten et al. | 435/221 |
| 6,190,900 | B1 * | 2/2001 | Sierkstra et al. | 435/221 |
| 6,197,567 | B1 * | 3/2001 | Aaslyng et al. | 435/221 |
| 6,218,165 | B1 | 4/2001 | Estell et al. | |
| 6,300,116 | B1 * | 10/2001 | von der Osten et al. | 435/220 |
| 6,376,450 | B1 | 4/2002 | Ghosh et al. | |
| 6,461,849 | B1 | 10/2002 | Olsen et al. | |
| 6,599,730 | B1 | 7/2003 | Brode et al. | |
| 6,773,907 | B2 | 8/2004 | Hansen et al. | |
| 6,902,922 | B2 | 6/2005 | Ness et al. | |
| 6,929,939 | B2 | 8/2005 | Estell et al. | |
| 7,306,937 | B2 | 12/2007 | Poulose et al. | |

(Continued)

FOREIGN PATENT DOCUMENTS

| | | |
|---|---|---|
| WO | WO 92/10755 | 6/1992 |
| WO | WO 99/53038 | 10/1999 |

(Continued)

OTHER PUBLICATIONS

Betzel et al, Journal of Molecular Biology, vol. 223, pp. 427-445 (1992).

*Primary Examiner* — Manjunath Rao
*Assistant Examiner* — William W Moore
(74) *Attorney, Agent, or Firm* — Kristin J. McNamara

(57) ABSTRACT

The present invention relates to subtilase subtilases with an altered immunogenicity, particularly subtilases with a reduced allergenicity. Furthermore, the invention relates to expression of said subtilase variants and subtilases and to their use, such as in detergents and oral care products.

5 Claims, 6 Drawing Sheets

Specific IgE-responses at day 31

U.S. PATENT DOCUMENTS

| | | | | |
|---|---|---|---|---|
| 7,824,896 | B2 * | 11/2010 | Minning et al. | 435/221 |
| 2003/0199077 | A1 * | 10/2003 | Fano et al. | 435/263 |
| 2004/0147008 | A1 | 7/2004 | Draborg et al. | |
| 2005/0009167 | A1 | 1/2005 | Weber et al. | |

FOREIGN PATENT DOCUMENTS

| | | |
|---|---|---|
| WO | WO 00/22103 | 4/2000 |
| WO | WO 00/26230 | 5/2000 |
| WO | WO 00/37599 | 6/2000 |
| WO | WO 01/07578 | 2/2001 |
| WO | WO 02/16547 | 2/2002 |
| WO | WO 03/057246 | 7/2003 |
| WO | WO 2004/003186 | 1/2004 |

* cited by examiner

Specific IgE-responses at day 31

Specific IgE-responses at day 31

Specific IgE-responses at day 31

Specific IgE-responses at day 31

M-CSF-enzyme dose/response curve

Alignment Mature BPN′ and Savinase®

```
BPN'_       AQSVPYGVSQ IKAPALHSQG YTGSNVKVAV IDSGIDSSHP DLKVAGGASM
Savinase    AQSVPWGISR VQAPAAHNRG LTGSGVKVAV LDTGI-STHP DLNIRGGASF

            51                                                  100
BPN'        VPSETNPFQD NNSHGTHVAG TVAALNNSIG VLGVAPSASL YAVKVLGADG
Savinase    VPGEP-STQD GNGHGTHVAG TIAALNNSIG VLGVAPSAEL YAVKVLGASG

           101                                                  150
BPN'        SGQYSWIING IEWAIANNMD VINMSLGGPS GSAALKAAVD KAVASGVVVV
Savinase    SGSVSSIAQG LEWAGNNGMH VANLSLGSPS PSATLEQAVN SATSRGVLVV

           151                                                  200
BPN'        AAAGNEGTSG SSSTVGYPGK YPSVIAVGAV DSSNQRASFS SVGPELDVMA
Savinase    AASGNSGA-G SIS---YPAR YANAMAVGAT DQNNNRASFS QYGAGLDIVA

           201                                                  250
BPN'        PGVSIQSTLP GNKYGAYNGT SMASPHVAGA AALILSKHPN WTNTQVRSSL
Savinase    PGVNVQSTYP GSTYASLNGT SMATPHVAGA AALVKQKNPS WSNVQIRNHL

           251                             275
BPN'        ENTTTKLGDS FYYGKGLINV QAAAQ
Savinase    KNTATSLGST NLYGSGLVNA EAATR
```

Fig. 4

SUBTILASE VARIANTS HAVING ALTERED IMMUNOGENICITY

CROSS-REFERENCE TO RELATED APPLICATIONS

This application is a continuation of U.S. application Ser. No. 11/547,555 filed on Oct. 24, 2006 (now U.S. Pat. No. 7,824,896), which is a 35 U.S.C. 371 national application of PCT/DK2005/000225 filed Apr. 1, 2005, which claims priority or the benefit under 35 U.S.C. 119 of Danish application no. PA 2004 00535 filed Apr. 2, 2004 and U.S. provisional application No. 60/564,131 filed Apr. 21, 2004, the contents of which are fully incorporated herein by reference.

FIELD OF INVENTION

The present invention relates to subtilase variants having altered immunogenicity, to the use thereof, as well as to a method for producing said subtilases and subtilase variants.

BACKGROUND OF THE INVENTION

An increasing number of proteins, including enzymes, are being produced industrially, for use in various industries, housekeeping and medicine. Being proteins they are likely to stimulate an immunological response in man and animals, e.g. an allergic response.

Various attempts to alter the immunogenicity of proteins have been conducted. In general it is only localized parts of the protein, known as epitopes, which are responsible for induction of an immunologic response. An epitope consist of a number of amino acids, which may in the primary sequence be sequential but which more often are located in proximity of each other in the 3-dimensional structure of the protein. It has been found that small changes in an epitope may affect the binding to an antibody. This may result in a reduced importance of such an epitope, maybe converting it from a high affinity to a low affinity epitope, or maybe even result in epitope loss, i.e. that the epitope cannot sufficiently bind an antibody to elicit an immunogenic response.

Another method for altering the immunogenicity of a protein is by masking the epitopes by e.g. adding compounds, such as PEG, to the protein.

WO 00/26230 and WO 01/83559 disclose two different methods of selecting a protein variant having reduced immunogenicity as compared to the parent protein.

WO 99/38978 discloses a method for modifying allergens to be less allergenic by modifying the IgE binding sites.

WO 99/53038 discloses mutant proteins having lower allergenic response in humans and methods for constructing, identifying and producing such proteins.

Subtilases, which have a wide-spread use within the detergent industry, is a group of enzymes which potentially may elicit an immunogenic response, such as allergy. Thus there is a constant need for subtilases or subtilase variants which have an altered immunogenicity, particularly a reduced allergenicity and which at the same still maintain the enzymatic activity necessary for their application.

WO 00/22103 discloses polypeptides with reduced immune response and WO 01/83559 discloses protein variants having modified immunogenicity.

BRIEF DESCRIPTION OF THE INVENTION

In a first aspect, the present invention relates to variants of the parent subtilase enzyme of SEQ ID NO. 1, or a subtilase having at least 80% homology, preferably 85%, or 90%, or 95%, or 98%, or 99% homology to the parent enzyme, the variants having altered immunogenicity as compared to the parent subtilase enzyme. The amino acid sequence of the variants differ from the amino acid sequence of the parent subtilase enzyme with respect to at least two mutations, at least one of the mutations occurring in one of four identified epitopes of the parent subtilase enzyme.

In a second aspect, the present invention relates to a variant of the subtilase of SEQ ID NO. 1, wherein Glutamic acid has been inserted after position 99 (*99aE).

In a third aspect, the present invention relates to variants of SEQ ID NO. 1, wherein two or more mutations occur in the identified epitopes. The said mutations may occur in combination with the insertion of Glutamic acid after position 99 (*99aE).

In a fourth aspect, the present invention relates to variants of SEQ ID NO. 1 wherein mutations outside the epitopes occurs at one or more of the positions 22, 141, 191, 247, 252, and 259. The said mutations may occur in combination with the insertion of Glutamic acid after position 99 (*99aE).

In a fifth aspect, the present invention relates variants from the group consisting of S57P+*99aE+R247Q, and *99aE+A158V, and *99aE+E136G, and *99aE+E136K, and I79T+*99aE+Q191E, and *99aE+S141N+S156D, and T58A+*99aE+S156N, and *99aE+S141G+S156N+Q191E, and S78P+*99aE+N185S+Q206L, and *99aE+G195P+T260L, and *99aE+G160S+G211S+T260N, and *99aE+G195D+G211N+T260L, and *99aE+G160S+G195P+G211S+T260N, and *99aE+A158N+S161D, and *99aE+S259N+T260I, and *99aE+S259N, and *99aE+S259R, and T22A+*99aE+G160N+T260L, and *99aE+G160D+G195P+G211P+T260N, and *99aE+G160S+G211D+T260L.

In a sixth aspect, the present invention relates to variants of SEQ ID NO. 1 with reduced immunogenicity as measured by epithelia assay.

In a seventh aspect, the present invention relates to variants of SEQ ID NO. 1 with reduced immunogenicity as measured by MINT studies or by C-ELISA.

In still further aspects, the present invention relates to a DNA sequence encoding a subtilase and/or a subtilase variant of the present invention and to a vector comprising said DNA sequence, and to a host cell comprising said vector.

In a final aspect, the present invention relates to a composition comprising a subtilase and/or a subtilase variant of the present invention.

DEFINITIONS

The term "subtilase" is in the context of the present invention to be understood as a sub-group of serine proteases as described by Siezen et al., *Protein Engng.* 4 (1991) 719-737 and Siezen et al. *Protein Science* 6 (1997) 501-523.

pIg is shorthand for a mixture of poly Immunoglobulins.

The term "parent" is in the context of the present invention to be understood as a protein, which is modified to create a protein variant. The parent protein may be a naturally occurring (wild-type) polypeptide or it may be a variant thereof prepared by any suitable means. For instance, the parent protein may be a variant of a naturally occurring protein which has been modified by substitution, chemical modification, deletion or truncation of one or more amino acid residues, or by addition or insertion of one or more amino acid residues to the amino acid sequence, of a naturally-occurring polypeptide. Thus the term "parent subtilase" refers to a subtilase which is modified to create a subtilase variant.

The term "variant" is in the context of the present invention to be understood as a protein which has been modified as compared to a parent protein at one or more amino acid residues.

The term "mutation(s)", "modification(s)" or "modified" is in the context of the present invention to be understood as to include chemical modification of a protein as well as genetic manipulation of the DNA encoding a protein. The modification(s) may be replacement(s) of the amino acid side chain(s), substitution(s), deletion(s) and/or insertions in or at the amino acid(s) of interest. Thus the term "modified protein", e.g. "modified subtilase", is to be understood as a protein which contains modification(s) compared to a parent protein.

The term "position" is in the present invention to be understood as the number from the N-terminal end of an amino acid in a protein. The position numbers used in the present invention refer to the positions of Subtilisin Novo (BPN') (SEQ ID NO: 5) from *B. amyloliquefaciens*. However, other subtilases are also covered by the present invention. The corresponding positions of other subtilases are defined by alignment with Subtilisin Novo (BPN') (SEQ ID NO: 5) from *B. amyloliquefaciens* by using the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). Unless specified, positions mentioned in the present invention, are given in the BPN' numeration, and can be converted by alignment.

The term "protein" is in the context of the present invention intended to cover oligopeptides, polypeptides as well as proteins as such.

The term "deletion" or "deleted", used in relation to a position or an amino acid, refers in the context of the present invention to that the amino acid in the particular position has been deleted or that it is absent.

The term "insertion" or "inserted", used in relation to a position or amino acid, refers in the context of the present invention to that 1 or more amino acids, e.g. between 1-5 amino acids, have been inserted or that 1 or more amino acids, e.g. between 1-5 amino acids are present after the amino acid in the particular position The term "substitution" or "substituted", used in relation to a position or amino acid, refers in the context of the present invention to that the amino acid in the particular position has been replaced by another amino acid or that an amino acid different from the one of a specified protein, e.g. protein sequence, is present.

Amino Acids

The well-known three-letter and one-letter abbreviations for amino acids is used (see e.g. Creighton T E (1993), Proteins; Structures and Molecular Properties, 2$^{nd}$ Edition W.H: Freeman and Company, figure 1.1, p. 3). The abbreviation "X" or "Xaa" is used for any amino acid. Within the context of the present invention the abbreviation "aa" is used for "amino acid".

Variants

To describe a deletion, an insertions and/or a substitution of amino acid(s) the following nomenclature is used in the present invention.

Original amino acid(s), position(s), deleted/inserted/substituted amino acid(s)

According to this the substitution of Glutamic acid for glycine in position 195 is designated as:

Gly 195 Glu or G195E a deletion of glycine in the same position is:

Gly 195* or G195*

Where a deletion in comparison with the sequence used for the numbering is indicated, an insertion in such a position is indicated as:

*36 Asp or *36D for insertion of an aspartic acid in position 36.

Insertion of an additional amino acid residue such as Aspartic acid is indicated as:

*36a Asp or *36aD for insertion of an aspartic acid just after position 36 in the parent protein.

Multiple mutations are separated by pluses, i.e.:

Arg 170 Tyr+Gly 195 Glu or R170Y+G195E representing mutations in positions 170 and 195 substituting tyrosine and glutamic acid for arginine and glycine, respectively.

Multiple mutations may also be separated by commas, i.e.:

Arg 170 Tyr, Gly 195 Glu or R170Y,G195E representing mutations in positions 170 and 195 substituting tyrosine and glutamic acid for arginine and glycine, respectively.

The "immunogenicity" of a compound used in connection with the present invention refers to the ability of this compound to induce an 'immunological response' in animals including man. The term "immunological response", used in connection with the present invention, is the response of an organism to a compound, which involves the immune system according to any of the four standard reactions (Type I, II, III and IV according to Coombs & Gell).

The immunogenicity can be assessed by animal experiments (e.g. MINT, and SC-mouse); C-ELISA (competitive ELISA) and epithelia cell assay are other predictors of immunogenicity The "allergenicity" of a compound used in connection with the present invention refers to the ability of this compound to induce an 'allergic response' in animals including man.

The term "allergic response", used in connection with the present invention, is the response of an organism to a compound, which involves IgE mediated responses (Type I reaction according to Coombs & Gell). It is to be understood that sensitisation (i.e. development of compound-specific IgE antibodies) upon exposure to the compound is included in the definition of "allergic response".

"Homology" or "homologous to" is in the context of the present invention to be understood in its conventional meaning and number the "homology" between two amino acid sequences should be determined by use of the "Similarity" defined by the GAP program from the University of Wisconsin Genetics Computer Group (GCG) package using default settings for alignment parameters, comparison matrix, gap and gap extension penalties. Default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, Journal of Molecular Biology, 48, 443-445 (1970). Identities can be extracted from the same calculation. The homology between two amino acid sequences can also be determined by "identity" or "similarity" using the GAP routine of the GCG package version 9.1 with default setting for alignment parameters, comparison matrix, gap and gap extension penalties can also be applied on subtilases using the following parameters: gap creation penalty=8 and gap extension penalty=8 and all other parameters kept at their default values. The output from the routine is besides the amino acid alignment the calculation of the "Percent Identity" and the "Similarity" between the two sequences. The numbers calculated using GCG package version 9.1 is slightly different from the version 8.

BRIEF DESCRIPTION OF THE DRAWINGS

FIG. 4 shows an alignment between subtilisin BPN' (a) and Savinase (SEQ ID NO 1). The alignment can be obtained by the GAP routine of the GCG package version 9.1 to number the variants using the following parameters: gap creation penalty=8 and gap extension penalty=8 and all other parameters kept at their default values.

SEQUENCE LISTING

Figure 1:
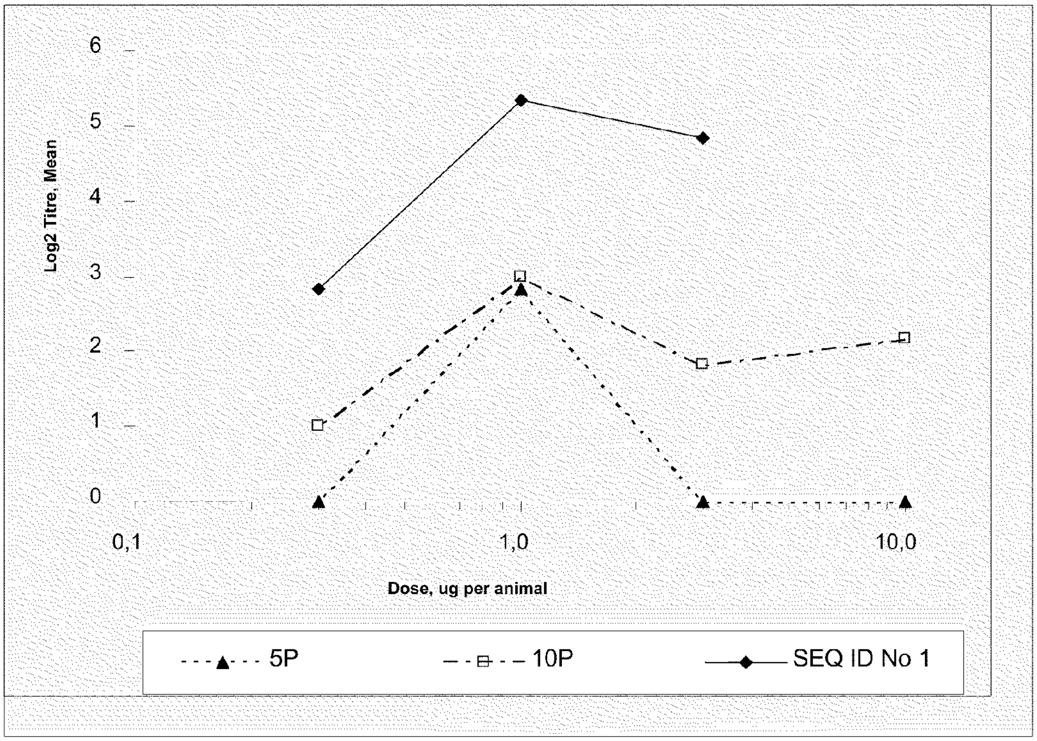
FIG. 1 shows the specific IgE-response at day 31 following Intranasal Instillation of the subtilase of SEQ ID NO 1 and two of the subtilases of the present invention (5P and 10P) into BDF1 mice, group mean values.
Figure 2A:
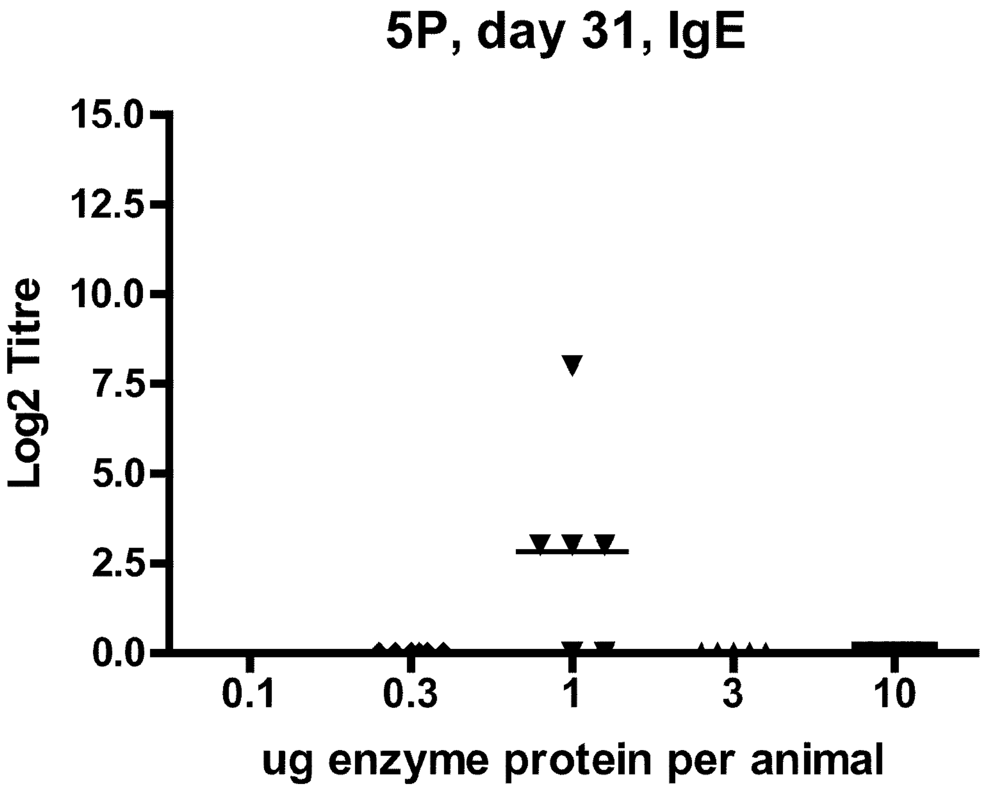
FIGS. 2*a-c* show individual values of the specific IgE-responses at day 31 following Intranasal Instillation of the subtilase of SEQ ID NO 1 and of two of the subtilases of the present invention (5P and 10P) into BDF1 mice.
Figure 2B:
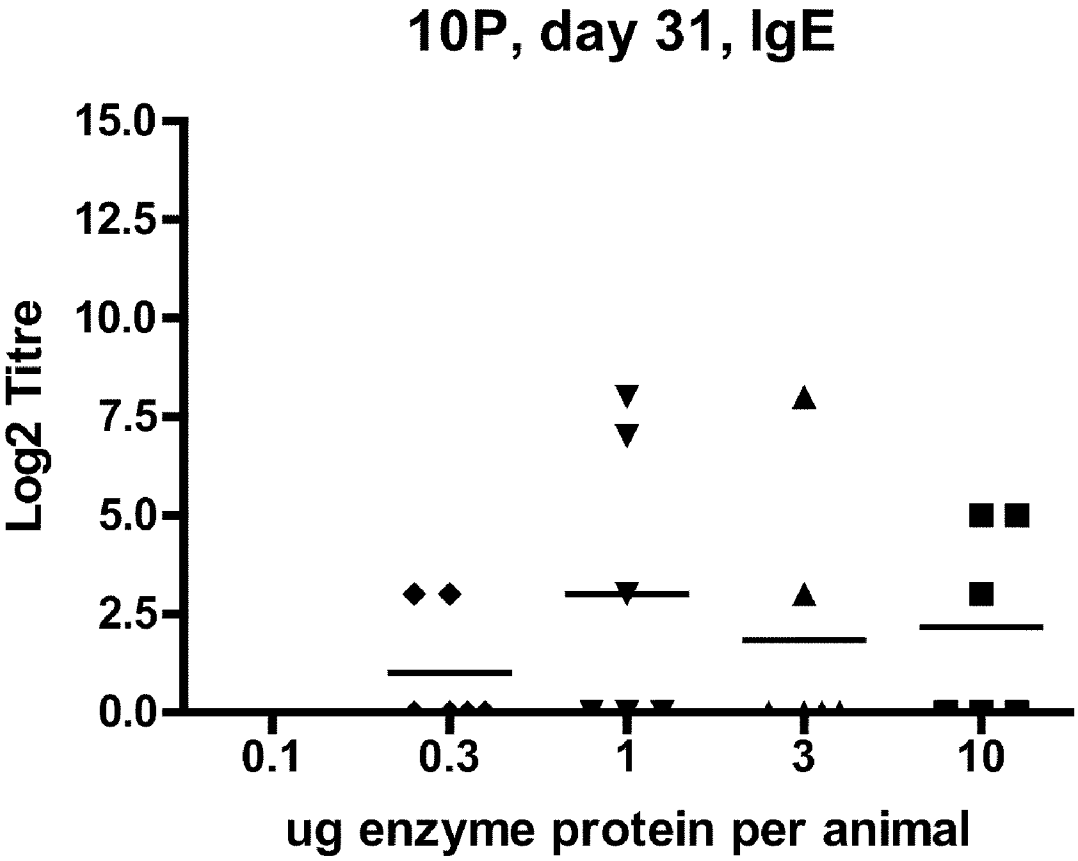
Figure 2C:
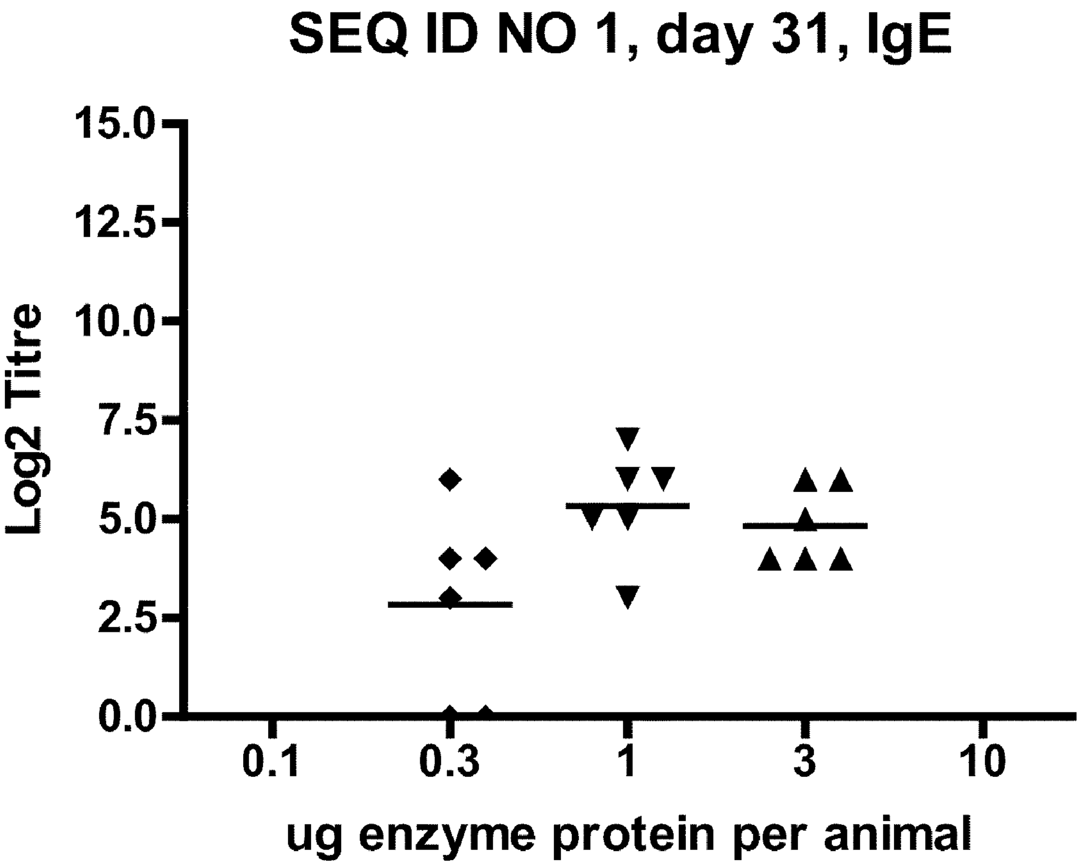

The present application contains information in the form of a sequence listing, which is appended to the application and also submitted on a data carrier accompanying this application. The contents of the data carrier are fully incorporated herein by reference.

DETAILED DESCRIPTION OF THE INVENTION

Subtilase Variants of the Invention

The present invention relates to subtilase variants of SEQ ID NO 1 (Savinase), wherein two or more mutations have been introduced, with at least one of the mutations in one of the four epitopes of the parent subtilase. The inventors have found that said subtilase variants have an altered immunogenicity in comparison to the parent subtilase (Savinase).

The amino acids in positions of a subtilase variant of the present invention may be modified by genetic manipulation of the DNA encoding the parent subtilase. In particular said positions may be modified by genetic manipulation of the DNA encoding the parent subtilase, e.g. by deletion, insertion or substitution. A mutation may typically involve modification of between 1 to 5 amino acids, such as 1, 2, 3, 4 or 5 amino acids.

Mutations may occur in between 1 to 4 epitopes, such as 1, 2, 3, or 4 epitopes.

In a particular embodiment of the invention, one of the mutations is the insertion of Glutamic acid (E) after position 99 (mutation stated as *99aE). Further mutations outside the epitopes may occur at one or more of the positions 22 (for example substitution with Alanine (T22A)), 141 (for example substitution with Asparagine (S141N) or Glycine (S141G)), 191 (for example substitution with Glutamic acid (Q191E)), and 247 (for example substitution with Glutamine (R247Q)).

In another particular embodiment of the invention, one may create libraries of genes that have been modified in one or more of the epitopes in a stochastic manner, e.g. such that several of the amino acids occurring in epitopes have been diversified by doped oligomer mutagenesis. Such libraries can then be screened for active variants (e.g. by plating transformed *Bacillus* colonies on skim-milk and growth media-containing agar plates) and the clones that express an active variant selected for sequencing of the relevant variant gene.

Mutations in the epitopes may occur at one or more of the positions 57, 58, and 136, wherein when a substitution occurs at position 57 the substituting amino acid may be Proline; when a substitution occurs at position 58 the substituting amino acid may be Alanine, and when a substitution occurs at position 136 the substituting amino acid may be selected from the group consisting of Glycine, and Lysine; or mutations in the epitopes may occur at one or more of the positions 156, 158, 160, 161, and 195, wherein when a substitution occurs at position 156 the substituting amino acid may be selected from the group consisting of Aspartic acid, and Asparagine; when a substitution occurs at position 158 the substituting amino acid may be selected from the group consisting of Valine, and Asparagine; when a substitution occurs at position 160 the substituting amino acid may be selected from the group consisting of Serine, Asparagine, and Aspartic Acid; when a substitution occurs at position 161 the substituting amino acid may be Aspartic Acid; when a substitution occurs at position 195 the substituting amino acid may be Glutamic acid; or mutations in the epitopes may occur at one or more of the positions 78, 79, 206, and 211, wherein when a substitution occurs at position 78 the substituting amino acid may be Proline; when a substitution occurs at position 79 the substituting amino acid may be Threonine; when a substitution occurs at position 206 the substituting amino acid may be Leucine; when a substitution occurs at position 211 the substituting amino acid may be selected from the group consisting of Serine, Proline, and Aspartic acid; or mutations in the epitopes may occur at one or more of the positions 158, 160, 161, 185, 195, 259, and 260, wherein when a substitution occurs at position 158 the substituting amino acid may be selected from the group consisting of Valine, and Asparagine; when a substitution occurs at position 160 the substituting amino acid may be selected from the group consisting of Serine, Asparagine, and Aspartic Acid; when a substitution occurs at position 161 the substituting amino acid may be Aspartic Acid; when a substitution occurs at position 185 the substituting amino acid may be Serine; when a substitution occurs at position 195 the substituting amino acid may be Glutamic acid; when a substitution occurs at position 259 the substituting amino acid may be selected from the group consisting of Asparagine, and Arginine; when a substitution occurs at position 260 the substituting amino acid may be selected from the group consisting of Leucine, Isoleucine, and Asparagine.

In particular the subtilase variant of the present invention may be one of the following: I79T+*99aE+Q191E; and *99aE+G195P+T260L; and *99aE+G160D+G195P+G211P+T260N.

In another particular embodiment, the present invention relates to variants with improved wash performance.

In a further embodiment, the present invention relates to expression of subtilase variants of the present invention.

In yet another embodiment, the present invention relates to compositions, in particular cleaning and personal care compositions, comprising a subtilase variant of the present invention.

Subtilase

Subtilases constitute a sub-group of serine protease according to Siezen et al., *Protein Engng.* 4 (1991) 719-737 and Siezen et al. *Protein Science* 6 (1997) 501-523. Subtilases are defined by homology analysis of more than 170 amino acid sequences of serine proteases previously referred to as subtilisin-like proteases. The subtilases may be divided into 6 sub-divisions, i.e. the Subtilisin family, the Thermitase family, the Proteinase K family, the Lantibiotic peptidase family, the Kexin family and the Pyrolysin family. The Subtilisin family may be further divided into 3 sub-groups, i.e. I-S1 ("true" subtilisins), I-S2 (highly alkaline proteases) and intracellular subtilisins. Definitions or grouping of enzymes may vary or change, however, in the context of the present invention the above division of subtilases into sub-division or sub-groups shall be understood as those described by Siezen et al., *Protein Engng.* 4 (1991) 719-737 and Siezen et al. *Protein Science* 6 (1997) 501-523.

The subtilase variants of the present invention are obtained by modification of the parent subtilase of SEQ ID NO. 1 or a subtilase having at least 80% homology, preferably 85%, or 90%, or 95%, or 98%, or 99% homology to the parent subtilase of SEQ ID NO. 1.

The parent subtilase and/or the subtilase of the present invention may be a subtilase isolated from natural source, i.e. a wild type subtilase, or it may be a subtilase isolated from a natural source in which subsequent modifications have been made while retaining the characteristic of a subtilase. Examples of such subtilase variants which may be parent subtilases include those disclosed in EP 130.756, EP 214.435, WO 87/04461, WO 87/05050, EP 251.446, EP 260.105, WO 88/08028, WO 88/08033, WO 89/06279, WO 91/00345, EP 525 610 and WO 94/02618. In another embodiment the parent subtilase may be a subtilase which has been prepared by a DNA shuffling technique, such as described by J. E. Ness et al., Nature Biotechnology, 17, 893-896 (1999). Further, a parent subtilase may be constructed by standard techniques for artificial creation of diversity, such as by DNA shuffling of different subtilase genes (WO 95/22625; Stemmer W P C, Nature 370:389-91 (1994)).

The activity of subtilases and subtilase variants can be determined as described in "Methods of Enzymatic Analysis", third edition, 1984, Verlag Chemie, Weinheim, vol. 5.

In Silico Identification of Epitope Patterns and Epitopes in Subtilase Enzymes Subtilase enzymes may be epitope mapped using the proprietary in silico epitope mapping tool disclosed in detail in WO 00/26230 and WO 01/83559. In brief, this tool comprises a database of epitope patterns (determined from an input of peptide sequences, known to bind specifically to anti-protein antibodies) and an algorithm to analyse 3-D structure of a given protein against the epitope pattern database. This will determine the possible epitopes on that protein, and the preference of each amino acid in the protein sequence to be part of epitopes.

The term "epitope pattern" as used herein is to be understood as a consensus sequence of antibody binding peptides. An example is the epitope pattern A R R * R. The sign "*" in this notation indicates that the aligned antibody binding peptides included a non-consensus moiety between the second and the third arginine. That moiety may be any amino acid or a few amino acids or no amino acid. Epitope patterns are used to identify epitopes and minimal epitopes on complex antigens.

Identifying Antibody-Binding Peptides

Antibody-binding peptides can be identified by many different ways. One is to synthesize a number of peptides of known sequence, and test for their ability to bind antibodies of interest, e.g., in ELISA or other immunochemical assays. Such data are available in great abundance in the literature.

A particularly effective way is to prepare a library of many different random peptide sequences and select experimentally only the ones that bind antibodies well and specific (i.e., can compete out the protein towards which the antibodies were raised). Phage display techniques are well suited for this way of finding antibody binding peptides:

In a phage display system, a sequence encoding a desired amino acid sequence is incorporated into a phage gene coding for a protein displayed on the surface of the phage. Thus, the phage will make and display the hybrid protein on its surface, where it can interact with specific target agents. Given that each phage contains codons for one specific sequence of a determined length, an average phage display library can express $10^8$-$10^{12}$ different random sequences. If the displayed sequence resembles an epitope, the phage can be selected by an epitope-specific antibody. Thus, it is possible to select specific phages from the bulk of a large number of phages, each expressing their one hybrid protein.

It is important that the amino acid sequence of the (oligo) peptides presented by the phage display system have a sufficient length to present a significant part of an epitope to be identified. The oligopeptides may have from 5 to 25 amino acids, preferably at least 8 amino acids, such as 9 amino acids.

The antibodies used for reacting with the oligopeptides can be polyclonal or monoclonal. In particular, they may be IgE antibodies to ensure that the epitopes identified are IgE epitopes, i.e., epitopes inducing and binding IgE. The antibodies may also be monospecific, meaning they are isolated according to their specificity for a certain protein. Polyclonal antibodies are preferred for building up data on antibody-binding peptides to be used in the in silico mapping tool in order to obtain a broader knowledge about the epitopes of a polypeptide.

These reactive peptides, by virtue of their reactivity against antibodies, to some degree resemble the appearance of an epitope on a full polypeptide.

Identifying Epitope Patterns from Reactive Peptides

The reactive (oligo)peptides identified e.g. by phage display are compared and aligned in order to identify common epitope patterns, which then can be used for identification of antibody binding epitopes on a 3-dimensional polypeptide.

In the alignment conservative alternatives to an amino acid such as Aspartate and Glutamate, Lysine and Arginine, Serine and Threonine are considered as one or equal. Thus, the alignment results in a number of patterns, which depend on the chosen number of residues of the peptides. Using for example a 7-mer peptide, the pattern may have the form:

X X * * X X X, where "*" in this notation indicates a non-consensus moiety which may be any amino acid or group of amino acids or no amino acid, while X is one of the following 13 residue types: AG, C, DE, FY, H, IL, KR, M, NQ, P, ST, V, and W, where the pairs AG, DE, FY, IL, KR, NQ, ST are conservative alternatives and considered equal. Accordingly, 3 peptides such as <u>A K S</u> N <u>N K R</u> (SEQ ID NO: 2)

<u>A K S</u> M <u>N K R</u> (SEQ ID NO: 3)

<u>A K T</u> P <u>N K K</u> (SEQ ID NO: 4)

would create a pattern of [AG] [KR] [ST] * [NQ] [KR] [KR], where the residues AG KR ST and NQ KR KR are consensus residues shared by all 3 peptides and thus the epitope pattern would be AG KR ST * NQ KR KR. The patterns are chosen to describe a complete set of reactive (oligo)peptides (obtained e.g., by a phage display and antibody reaction) by the fewest possible patterns.

The epitope patterns may be determined directly from the reactive peptides; if for example a library of 7-mer reactive peptides is made, one can use each different reactive 7mer peptide, taking conservative alternatives into account, as an epitope pattern in the epitope mapping approach as described below.

It is also possible to reduce the number of epitope patterns to be examined in the epitope mapping by removing redundant patterns and/or by employing experimental designs as known in the art (See example 1).

Epitope Mapping Algorithm

When epitope patterns have been identified they are subsequently compared to the three-dimensional coordinates of the amino acid sequence of the polypeptide of interest, in order to identify combinations of residues on the polypeptide surface corresponding to the consensus sequence(s) or epitope pattern(s). In this way, amino acids residues, which are important for antibody binding, can be identified.

Once one or more epitope patterns have been identified, any polypeptide for which a three-dimensional structure is known may be analysed for epitopes matching the epitope patterns. Finding an epitope on a polypeptide is achieved by searching the surface of the polypeptide in the following way:

(1) For all amino acids in the polypeptide it is examined if (a) the amino acid type match the first amino acid of an epitope pattern and (b) the surface accessibility greater than or equal to a chosen threshold allowing the amino acid to be immunological interactive. Those amino acid satisfying 1(a) and 1(b) are selected.

(2) For all amino acids within a selected distance (e.g. 10 Angstroms) of the amino acids selected in step 1 it is examined if (a) the amino acid type matches the second amino acid of the pattern and (b) the surface accessibility greater than or equal to a chosen threshold allowing the amino acid to be immunological interactive. Those amino acid satisfying 2(a) and 2(b) are selected (3) For all amino acids within a selected distance (e.g. 10 Angstroms) of the amino acids selected in step 2 it is examined if (a) the amino acid type matches the third amino acid of the pattern and (b) the surface accessibility greater than or equal to a chosen threshold allowing the amino acid to be immunological interactive. Those amino acid satisfying 3(a) and 3(b) are selected.

This procedure (step 3) is repeated for all amino acids in the epitope pattern consensus sequence. The coordinates of its C-alpha atom define the spatial positioning of an amino acid. The surface solvent accessibility threshold is given in percent of an average for the particular residue type (see example 1).

If matching amino acids for all amino acids in the epitope pattern can be found in the structure of the polypeptide it is a very strong indication that an epitope has been found.

However it is also checked that the size of the epitope is satisfactory, i.e., the distance between any two residues is below a given threshold, usually 25 Å.

The epitopes found may be ranked and weighted according to their total accessible surface area, in order to improve further the predictability of the tool.

Finally, when all possible epitopes have been mapped for the protein of interest, one can provide a score for each amino acid of the protein by adding up the number of times it appears in an epitope pattern. This score will be an indication of the likelihood that modification (substitution, insertion, deletion, glycosylation or chemical conjugation) of that amino acid will, result in a variant with a lower antigenicity. All amino acids of the protein can then be ranked according to this score and those with highest scores can be selected for mutagenesis.

The epitope mapping tool can be adjusted, such that only a subset of the known reactive peptides are included as data set for building epitope patterns, and thus for conducting epitope mapping. For instance, one may choose only to include peptides reactive to IgE antibodies (rather than to IgG or other antibodies), or one may include only peptides reactive to human antibodies etc. One may choose to involve only peptides reactive against the target protein in order to get a more specific response, however, in general, peptides reactive to antibodies that in turn were raised against any protein are included.

If no three-dimensional structure coordinates are available for the protein of interest, one can map the epitope patterns directly to the primary sequence of the protein of interest.

From all the above information, it is obvious, that the epitopes are conveniently determined using this epitope mapping tool.

Further, the in silico epitope mapping tool can be used to predict if mutating one amino acid residue will result in that the new variant overall will have fewer epitopes. Thus, some or all 19 possible substitutions can be tested in a given position, the epitope mapping procedure repeated for a model structure of each of these proposed variants, and the best variant(s) can be constructed by mutation and tested experimentally.

Identified Epitopes of Parent Subtilase

Using the epitope mapping tool the present inventors have identified four epitopes corresponding to the following positions of SEQ ID NO 1:

Epitope 1: P52-N62; A98-S105; G127-E136; Y167; R170.

Epitope 2: G127; P129; N155-S161; Y167; R170; S188; Y192-G195; N218; N261-L262.

Epitope 3: A1-W6; P14-N18; T38-I44; Q59-N62; L75-I79; S87; N155; N204-N218.

Epitope 4: N6; Q12; G157-S161; D181-N185; Y192-G195; T255-S265.

Selection of Positions for Mutation

Once the epitopes of a polypeptide have been determined, variants of the polypeptide with modified antigenic properties can be made by mutating one or more of the amino acid residues comprised in the epitope. In this context mutation encompasses deletion and/or substitution of an amino acid residue and/or insertion of one or more amino acids before or after that residue.

When providing a polypeptide variant suitable as an enzyme, it is particularly desirable to alter IgE epitopes to reduce the binding of IgE, while at the same time maintaining the activity and stability of the variant, hence it is desirable that the polypeptides retains the three-dimensional conformation of the parent polypeptide.

The epitope identified may be mutated by substituting at least one amino acid of the epitope. The mutation will often be a substitution with an amino acid of different size, hydrophilicity, polarity and/or acidity, such as a small amino acid in exchange of a large amino acid, a hydrophilic amino acid in exchange of a hydrophobic amino acid, a polar amino acid in exchange of a non-polar amino acid and a basic in exchange of an acidic amino acid.

The mutation(s) performed may be performed by standard techniques well known to a person skilled in the art, such as site-directed mutagenesis (see, e.g., Sambrook et al. (1989), Molecular Cloning. A Laboratory Manual, Cold Spring Harbor, N.Y.).

The mutagenesis may be spiked mutagenesis which is a form of site-directed mutagenesis, in which the primers used have been synthesized using mixtures of oligonucleotides at one or more positions.

A general description of nucleotide substitution can be found in e.g., Ford et al., 1991, Protein Expression and Purification 2, pp. 95-107.

The subtilisin variant of the present invention concerns variant where at least one mutation is in one of the identified epitopes in order to alter the immunogenicity of the variant as compared to the parent subtilase. Particularly the variant has altered antibody binding profile as compared the parent subtilase, more particularly combined with preserved performance and/or activity and/or stability. Still more preferably, the variant has an altered immunogenic profile in exposed animals, including humans, as compared to the parent subtilase.

Further the variant induces an altered immunogenic response, preferably reduced allergenic response, in exposed animals, including humans, as compared to the parent subtilase.

Verification of Variants Having Altered Antigenic Properties

The mutation of amino acids, comprised in an epitope, will cause the antigenic properties of the polypeptide to change, as predicted by the in silico determination of the epitopes. However, the quantitative effect of the mutation on the antigenicity, i.e., the antibody binding, and the immunogenicity of the variant, is suitably determined using various in vivo or in vitro model systems. The subtilase variants of the present invention may be tested for altered allergenicity and/or immunogenicity by using a purified preparation of the subtilase variants. Thus before testing the subtilase variants for altered allergenicity and/or immunogenicity they may be expressed in larger scale and/or purified by conventional methods.

The antibody binding can be examined in detail using dose-response curves and e.g., direct or competitive ELISA (c-ELISA), such as described in WO 99/47680, or by other or other solid phase immunoassays or cellular assays.

In a particular embodiment the residual binding of the polypeptide variant is at least 5%, such as 10%, or 20%, or 30%, more preferably at least 40% such as 50%, or 60%, or 70%, most preferably at least 80%, such as 85%, or 90%, or 95%, or 98%, or 99%, or 100%.

In another particular embodiment the binding affinity is different from 1. The binding affinity may be lower than 1 when compared to a parent enzyme, such as lower than 0.9, such as 0.8, or 0.7, or 0.6, or lower than 0.5, such as 0.4, or 0.3, or 0.2, or lower than 0.15, such as 0.1, or 0.05, or 0.01. The binding affinity may also be higher than 1 when compared to a parent enzyme, such as higher than 1.5, or 2.0, or 3.0, or 4.0, or 5.0, or higher than 7.0, such as 10, or 15, or 20, or 30, or higher than 40, such as 50, or 60, or 70, or 80, or 90, or 100, or 150, or 200.

In a particular embodiment in vitro screening for reduced allergenicity and adjuvancy can be performed on a human airlifted epithelial cell culture assay. Human lung epithelial cells are seeded on polycarbonate tissue culture insert, placed in wells on a tissue culture plate. The cells are cultured until confluent. Then the medium in the insert is removed and the cells are cultured for 3 more days at the liquid-air interface thus created. The cells are then stimulated with increasing doses of enzyme for 4 hours. Then supernatants are harvested and M-CSF (Macrophage colony-stimulating factor) release triggered to enzyme in the supernatant is measured. Variants with reduced allergenicity and adjuvancy require higher doses in order to elicit comparable M-CSF responses with parent protein. The epithelial assay as described in Example 7 shows that M-CSF production by epithelial cells in response to stimulation with enzyme variants requires higher enzyme doses for elicitation of M-CSF responses that are comparable with parent protein (table 3). In particular the M-CSF release triggered to enzyme variants as compared with parent protein is reduced at least 2 times, preferably at least 5, 10, 25 times, or 40, 60, 80, 100 times, or even 150 or 200 times for enzyme variants with a reduced allergenic potency. In addition, the toxic potency of the variants determined by a fall in M-CSF release by epithelial cells when triggered by higher amounts of protease is reduced.

In a particular embodiment the in vivo verification comprises skin prick testing (SPT), in which a subtilase allergic subject/individual is exposed to Subtilase on the skin, followed by puncture with a needle, where after the IgE reactivity is measured as the diameter of the wheal and flare reaction, in response to a polypeptide variant of the invention is compared to that to the parent subtilase (Kronquist et al., Clin. Exp. Allergy, 2000, vol. 30, pp. 670-676).

The in vivo immunogenic properties of the polypeptide variant of the invention may also suitably be measured in an animal test, wherein test animals are exposed to a parent subtilase and the responses to variants as well as to the parent subtilase allergen are measured. The immune response measurements may include comparing reactivity of serum IgE or T-cells from a test animal with a parent subtilase and the subtilase variant.

In a particular embodiment the in vivo verification comprises exposing a mouse to a parent subtilase by the intranasal route, and verifying that serum IgE is less reactive with a subtilase variant than with the parent subtilase. Useful in vivo animal models include the mouse intranasal test (MINT) model (Robinson et al., Fund. Appl. Toxicol. 34, pp. 15-24, 1996). Thus the term reduced allergenicity used in connection with the subtilases variants/subtilases of the present invention is to be understood as an IgE response which is less or none in said assay compared to the parent subtilase. In particular the IgE level measured in said assay obtained in response to said subtilase variants and/or subtilases may be 35%, such as 30% or 25% or 20% or 15% or 10% of the IgE level obtained in response to the parent subtilase/Savinase, respectively.

Further the in vivo verification may comprise exposing a test animal to a polypeptide variant by the intratracheal route and verifying that the specific IgE titres or IgG titres if in guinea pigs are lower than with the parent subtilase. Useful in vivo animal models include the guinea pig intratracheal (GPIT) model (Ritz, et al. Fund. Appl. Toxicol., 21, pp. 31-37, 1993) and the rat intratracheal (rat-IT) model (WO 96/17929, Novo Nordisk).

Still further the in vivo verification may comprise exposing a test animal subcutaneously to the subtilase allergen and the polypeptide variant. Also, IgE binding and cross reactivity can be measured following this route of exposure. A suitable model is the mouse subcutaneous (mouse-SC) model (WO 98/30682, Novo Nordisk).

Methods for Production of Subtilase Variants and Subtilases

The subtilase variants and subtilases of the present invention may be produced by any known method within the art and the present invention also relates to nucleic acid encoding a subtilase variant or subtilase of the present invention, a DNA construct comprising said nucleic acid and a host cell comprising said nuclei acid sequence.

In general natural occurring proteins may be produced by culturing the organism expressing the protein and subsequently purifying the protein or it may be produced by cloning a nucleic acid, e.g. genomic DNA or cDNA, encoding the protein into an expression vector, introducing said expression vector into a host cell, culturing the host cell and purifying the expressed protein.

Typically protein variants may be produced by site-directed mutagenesis of a parent protein, introduction into expression vector, host cell etc. The parent protein may be cloned from a strain producing the polypeptide or from an expression library, i.e. it may be isolated from genomic DNA or prepared from cDNA, or a combination thereof.

In general standard procedures for cloning of genes and/or introducing mutations (random and/or site directed) into said genes may be used in order to obtain a parent subtilase, or subtilase or subtilase variant of the invention. For further description of suitable techniques reference is made to Molecular cloning: A laboratory manual (Sambrook et al. (1989), Cold Spring Harbor lab., Cold Spring Harbor, N.Y.; Ausubel, F. M. et al. (eds.)); Current protocols in Molecular Biology (John Wiley and Sons, 1995; Harwood, C. R., and Cutting, S. M. (eds.)); Molecular Biological Methods for *Bacillus* (John Wiley and Sons, 1990); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); A Practical Guide To Molecular Cloning (B. Perbal, (1984)) and WO 96/34946.

Expression Vectors

A recombinant expression vector comprising a nucleic acid sequence encoding a subtilase or subtilase variant of the invention may be any vector that may conveniently be subjected to recombinant DNA procedures and which may bring about the expression of the nucleic acid sequence.

The choice of vector will often depend on the host cell into which it is to be introduced. Examples of a suitable vector include a linear or closed circular plasmid or a virus. The vector may be an autonomously replicating vector, i.e., a vector which exists as an extra chromosomal entity, the replication of which is independent of chromosomal replication, e.g., a plasmid, an extra chromosomal element, a mini chromosome, or an artificial chromosome. The vector may contain any means for assuring self-replication. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes it function as temperature-sensitive in the host cell (see, e.g., Ehrlich, 1978, Proceedings of the National Academy of Sciences USA 75:1433).

Alternatively, the vector may be one which, when introduced into the host cell, is integrated into the genome and replicated together with the chromosome(s) into which it has been integrated. Vectors which are integrated into the genome of the host cell may contain any nucleic acid sequence enabling integration into the genome, in particular it may contain nucleic acid sequences facilitating integration into the genome by homologous or non-homologous recombination. The vector system may be a single vector, e.g. plasmid or virus, or two or more vectors, e.g. plasmids or virus', which together contain the total DNA to be introduced into the genome of the host cell, or a transposon.

The vector may in particular be an expression vector in which the DNA sequence encoding the subtilase of the invention is operably linked to additional segments or control sequences required for transcription of the DNA. The term, "operably linked" indicates that the segments are arranged so that they function in concert for their intended purposes, e.g. transcription initiates in a promoter and proceeds through the DNA sequence encoding the subtilase variant. Additional segments or control sequences include a promoter, a leader, a polyadenylation sequence, a propeptide sequence, a signal sequence and a transcription terminator. At a minimum the control sequences include a promoter and transcriptional and translational stop signals.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus subtilis* levansucrase gene (sacB), the *Bacillus stearothermophilus* maltogenic amylase gene (amyM), the *Bacillus licheniformis* alpha-amylase gene (amyL), the *Bacillus amyloliquefaciens* alpha-amylase gene (amyQ), the *Bacillus subtilis* alkaline protease gene, or the *Bacillus pumilus* xylosidase gene, the *Bacillus amyloliquefaciens* BAN amylase gene, the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75:3727-3731). Other examples include the phage Lambda $P_R$ or $P_L$ promoters or the *E. coli* lac, trp or tac promoters or the *Streptomyces coelicolor* agarase gene (dagA). Further promoters are described in "Useful proteins from recombinant bacteria" in Scientific American, 1980, 242:74-94; and in Sambrook et al., 1989, supra.

Examples of suitable promoters for use in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral (-amylase and *Aspergillus oryzae* triose phosphate isomerase), and glaA promoters. Further suitable promoters for use in filamentous fungus host cells are the ADH3 promoter (McKnight et al., The EMBO J. 4 (1985), 2093-2099) or the tpiA promoter.

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

Further useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423-488. In a mammalian host cell, useful promoters include viral promoters such as those from Simian Virus 40 (SV40), Rous sarcoma virus (RSV), adenovirus, and bovine papilloma virus (BPV).

Examples of suitable promoters for use in mammalian cells are the SV40 promoter (Subramani et al., Mol. Cell Biol. 1 (1981), 854-864), the MT-1 (metallothionein gene) promoter (Palmiter et al., Science 222 (1983), 809-814) or the adenovirus 2 major late promoter. An example of a suitable promoter for use in insect cells is the polyhedrin promoter (U.S. Pat. No. 4,745,051; Vasuvedan et al., FEBS Lett. 311, (1992) 7-11), the P10 promoter (J. M. Vlak et al., J. Gen. Virology 69, 1988, pp. 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

The DNA sequence encoding the subtilase or subtilase variant of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like ampicillin, kanamycin, chloramphenicol, erythromycin, tetracycline, spectinomycine, neomycin, hygromycin, methotrexate, or resistance to heavy metals, virus or herbicides, or which provides for prototrophy or auxotrophs. Examples of bacterial selectable markers are the dal genes from *Bacillus subtilis* or *Bacillus licheniformis*, resistance. A frequently used mammalian marker is the dihydrofolate reductase gene (DHFR). Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Particularly, for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by cotransformation, e.g., as described in WO 91/17243, where the selectable marker is on a separate vector.

To direct a subtilase or subtilase variant of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al.).

More than one copy of a nucleic acid sequence encoding an enzyme of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

Host Cells

The DNA sequence encoding the subtilases and/or subtilase variants of the present invention may be either homologous or heterologous to the host cell into which it is introduced. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present subtilases and/or subtilase variants, such as prokaryotes, e.g. bacteria or eukaryotes, such as fungal cells, e.g. yeasts or filamentous fungi, insect cells, plant cells or mammalian cells.

Examples of bacterial host cells which, on cultivation, are capable of producing the subtilases or subtilase variants of the invention are gram-positive bacteria such as strains of *Bacillus*, e.g. strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of *Streptomyces*, such as *S. lividans* or *S. murinus*, or gram-negative bacteria such as *Escherichia coli* or *Pseudomonas* sp.

The transformation of the bacteria may be effected by protoplast transformation, electroporation, conjugation, or by using competent cells in a manner known per se (cf. Sambrook et al., supra).

When expressing the subtilases and/or subtilase variant in bacteria such as *E. coli*, the enzyme may be retained in the cytoplasm, typically as insoluble granules (known as inclusion bodies), or it may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the subtilases and/or subtilase variant in gram-positive bacteria such as *Bacillus* or *Streptomyces* strains, the enzyme may be retained in the cytoplasm, or it may be directed to the extracellular medium by a bacterial secretion sequence. In the latter case, the enzyme may be recovered from the medium as described below.

Examples of host yeast cells include cells of a species of *Candida, Kluyveromyces, Saccharomyces, Schizosaccharomyces, Candida, Pichia, Hansenula*, or *Yarrowia*. In a particular embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. Other useful yeast host cells are a *Kluyveromyces lactis Kluyveromyces fragilis Hansenula polymorpha, Pichia pastoris Yarrowia lipolytica, Schizosaccharomyces pombe, Ustilgo maylis, Candida maltose, Pichia guillermondii* and *Pichia methanolio* cell (cf. Gleeson et al., J. Gen. Microbiol. 132, 1986, pp. 3459-3465; U.S. Pat. No. 4,882,279 and U.S. Pat. No. 4,879,231). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast *Saccharomyces*, Strathern et al., editors, 1981). Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153:163; and Hinnen et al., 1978, Proceedings of the National Academy of Sciences USA 75:1920.

Examples of filamentous fungal cells include filamentous forms of the subdivision Eumycota and Oomycota (as defined by Hawksworth et al., 1995, supra), in particular it may of the a cell of a species of *Acremonium*, such as *A. chrysogenum, Aspergillus*, such as *A. awamori, A. foetidus, A. japonicus, A. niger, A. nidulans* or *A. oryzae, Fusarium*, such as *F. bactridioides, F. cerealis, F. crookwellense, F. culmorum, F. graminearum, F. graminum, F. heterosporum, F. negundi, F. reticulatum, F. roseum, F. sambucinum, F. sarcochroum, F. sulphureum, F. trichothecioides* or *F. oxysporum, Humicola*, such as *H. insolens* or *H. lanuginose, Mucor*, such as *M. miehei, Myceliophthora*, such as *M. thermophilum, Neurospora*, such as *N. crassa, Penicillium*, such as *P. purpurogenum, Thielavia*, such as *T. terrestris, Tolypocladium*, or *Trichoderma*, such as *T. harzianum, T. koningii, T. longibrachiatum, T. reesei* or *T. viride*, or a teleomorph or synonym thereof. The use of *Aspergillus* spp. for the expression of proteins is described in, e.g., EP 272 277, EP 230 023.

Examples of insect cells include a *Lepidoptera* cell line, such as *Spodoptera frugiperda* cells or *Trichoplusia ni* cells (cf. U.S. Pat. No. 5,077,214). Culture conditions may suitably be as described in WO 89/01029 or WO 89/01028. Transformation of insect cells and production of heterologous polypeptides therein may be performed as described in U.S. Pat. No. 4,745,051; U.S. Pat. No. 4,775,624; U.S. Pat. No. 4,879,236; U.S. Pat. No. 5,155,037; U.S. Pat. No. 5,162,222; EP 397,485).

Examples of mammalian cells include Chinese hamster ovary (CHO) cells, HeLa cells, baby hamster kidney (BHK) cells, COS cells, or any number of other immortalized cell lines available, e.g., from the American Type Culture Collection. Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Ausubel et al., Current Protocols in Molecular Biology, John Wiley and Sons, Inc., N.Y., 1987, Hawley-Nelson et al., Focus 15 (1993), 73; Ciccarone et al., Focus 15 (1993), 80; Graham and van der Eb, Virology 52 (1973), 456; and Neumann et al., EMBO J. 1 (1982), 841-845. Mammalian cells may be transfected by direct uptake using the calcium phosphate precipitation method of Graham and Van der Eb (1978, Virology 52:546).

Methods for Expression and Isolation of Proteins

To express an enzyme of the present invention the above mentioned host cells transformed or transfected with a vector comprising a nucleic acid sequence encoding an enzyme of the present invention are typically cultured in a suitable nutrient medium under conditions permitting the production of the desired molecules, after which these are recovered from the cells, or the culture broth.

The medium used to culture the host cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media may be prepared using procedures known in the art (see, e.g., references for bacteria and yeast; Bennett, J. W. and LaSure, L., editors, More Gene Manipulations in Fungi, Academic Press, CA, 1991).

If the enzymes of the present invention are secreted into the nutrient medium, they may be recovered directly from the medium. If they are not secreted, they may be recovered from cell lysates. The enzymes of the present invention may be recovered from the culture medium by conventional procedures including separating the host cells from the medium by centrifugation or filtration, precipitating the proteinaceous components of the supernatant or filtrate by means of a salt, e.g. ammonium sulfate, purification by a variety of chromatographic procedures, e.g. ion exchange chromatography, gel filtration chromatography, affinity chromatography, or the like, dependent on the enzyme in question.

The enzymes of the invention may be detected using methods known in the art that are specific for these proteins. These detection methods include use of specific antibodies, formation of a product, or disappearance of a substrate. For example, an enzyme assay may be used to determine the activity of the molecule. Procedures for determining various kinds of activity are known in the art.

The enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

When an expression vector comprising a DNA sequence encoding an enzyme of the present invention is transformed/transfected into a heterologous host cell it is possible to enable heterologous recombinant production of the enzyme. An advantage of using a heterologous host cell is that it is possible to make a highly purified enzyme composition, characterized in being free from homologous impurities, which are often present when a protein or peptide is expressed in a homologous host cell. In this context homologous impurities mean any impurity (e.g. other polypeptides than the enzyme of the invention) which originates from the homologous cell where the enzyme of the invention is originally obtained from.

Commercial Enzyme Applications

The present invention also relates to compositions comprising subtilase and/or subtilase variants of the present invention. For example the subtilase/subtilase variant may be used in compositions for personal care, such as shampoo, soap bars, skin lotion, skin cream, hair dye, toothpaste, contact lenses, cosmetics, toiletries, or in compositions used for treating textiles, for manufacturing food, e.g. baking or feed, or in compositions for cleaning purposes, e.g. detergents, dishwashing compositions or for cleaning hard surfaces.

Detergents

The subtilase and/or subtilase variant of the invention may for example be used in detergent composition. It may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid subtilase/subtilase variant preparations may, for instance, be stabilized by adding a polyol such as propylene glycol, a sugar or sugar alcohol, lactic acid or boric acid according to established methods. Other enzyme stabilizers are well known in the art. Protected subtilase/subtilase variants may be prepared according to the method disclosed in EP 238,216.

The detergent composition may be in any convenient form, e.g. as powder, granules, paste or liquid. A liquid detergent may be aqueous, typically containing up to 70% water and 0-30% organic solvent, or non-aqueous.

The detergent composition may comprise one or more surfactants, each of which may be anionic, nonionic, cationic, or zwitterionic. The detergent will usually contain 0-50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0-40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as e.g. proteases, amylases, lipolytic enzymes, cutinases, cellulases, peroxidases, oxidases, and further anti-microbial polypeptides.

The detergent may contain 1-65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The detergent composition may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7-11.

Dishwashing Composition

Furthermore, the subtilases and/or subtilase variants of the present invention may also be used in dishwashing detergents.

Dishwashing detergent compositions typically comprise a surfactant which may be anionic, non-ionic, cationic, amphoteric or a mixture of these types. The detergent may contain 0-90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1-90% of detergent builders.

Examples of phosphorus-containing inorganic alkaline detergent builders, when present, include the water-soluble salts especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulphonates, carboxymethoxy succinates, ammonium polyacetates, carboxylates, polycarboxylates, aminopolycarboxylates, polyacetyl carboxylates and polyhydroxsulphonates.

Other suitable organic builders include the higher molecular weight polymers and copolymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches may be in the form of an inorganic persalt, particularly with a bleach precursor or as a peroxy acid compound. Examples of suitable peroxy bleach compounds include alkali metal perborates, e.g. tetrahydrates and monohydrates, alkali metal percarbonates, persilicates and perphosphates. Particularly activator materials may be TAED and glycerol triacetate.

The dishwashing detergent composition may be stabilized using conventional stabilizing agents for enzymes, e.g. a polyol such as e.g. propylene glycol, a sugar or a sugar alcohol, lactic acid, boric acid, or a boric acid derivative, e.g. an aromatic borate ester.

The dishwashing detergent composition may also contain other conventional detergent ingredients, e.g. deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Finally, the subtilases and/or subtilase variants of the invention may be used in conventional dishwashing-detergents, e.g. in any of the detergents described in any of the following patent publications:

EP 518719, EP 518720, EP 518721, EP 516553, EP 516554, EP 516555, GB 2200132, DE 3741617, DE 3727911, DE 4212166, DE 4137470, DE 3833047, WO 93/17089, DE 4205071, WO 52/09680, WO 93/18129, WO 93/04153, WO 92/06157, WO 92/08777, EP 429124, WO 93/21299, U.S. Pat. No. 5,141,664, EP 561452, EP 561446, GB 2234980, WO 93/03129, EP 481547, EP 530870, EP 533239, EP 554943, EP 346137, U.S. Pat. No. 5,112,518, EP 318204, EP 318279, EP 271155, EP 271156, EP 346136, GB 2228945, CA 2006687, WO 93/25651, EP 530635, EP 414197, U.S. Pat. No. 5,240,632.

Personal Care Applications

Another useful application area for the subtilases and/or subtilase variants of the present invention is the personal care area where the end-user is in close contact with the protein, and where certain problems with allergenicity has been encountered in experimental setups (Kelling et al., J. All. Clin. Imm., 1998, Vol. 101, pp. 179-187 and Johnston et al., Hum. Exp. Toxicol., 1999, Vol. 18, p. 527).

First of all the conjugate or compositions of the invention can advantageously be used for personal care products, such as hair care and hair treatment products. This include products such as shampoo, balsam, hair conditioners, hair waving compositions, hair dyeing compositions, hair tonic, hair liquid, hair cream, hair rinse, hair spray.

Further contemplated are oral care products such as dentifrice, oral washes, chewing gum.

Also contemplated are skin care products and cosmetics, such as skin cream, skin milk, cleansing cream, cleansing lotion, cleansing milk, cold cream, cream soap, nourishing essence, skin lotion, milky lotion, calamine lotion, hand cream, powder soap, transparent soap, sun oil, sun screen, shaving foam, shaving cream, baby oil lipstick, lip cream, creamy foundation, face powder, powder eye-shadow, powder, foundation, make-up base, essence powder, whitening powder.

Also for contact lenses hygiene products the subtilases and/or subtilase variants of the invention may be used advantageously. Such products include cleaning and disinfection products for contact lenses.

Food and Feed

The subtilase variants and/or subtilases of the present invention may also be used in food or feed products. For example said subtilase variants/subtilases may be used modify the gluten phase of the dough, e.g. a hard wheat flour can be softened with a protease. Another example is within the brewery industry, where said subtilase variants/subtilases may be used for brewing with unmalted cereals and/or for controlling the nitrogen content.

Within the animal feed industry said subtilase variants and/or subtilases may be used for so to speak expanding the animals' digestion system.

Materials and Methods

Materials

ELISA Reagents:

Horse Radish Peroxidase labelled pIg anti-rabbit-Ig (Dako, DK, P217, dilution 1:1000).

Mouse anti-rat IgE (Serotec MCA193; dilution 1:200).

Biotin-labelled mouse anti-rat IgG1 monoclonal antibody (Zymed 03-9140; dilution 1:1000)

Biotin-labelled rat anti-mouse IgG1 monoclonal antibody (Serotec MCA336B; dilution 1:2000)

Streptavidin-horse radish peroxidase (Kirkegård & Perry 14-30-00; dilution 1:1000).

OPD: o-phenylene-diamine, (Kementec cat no. 4260)

Rabbit anti-Savinase polyclonal IgG prepared by conventional means

Rat anti-Savinase polyclonal IgE prepared by conventional means.

Buffers and Solutions:

| PBS (pH 7.2 (1 liter)) | |
|---|---|
| NaCl | 8.00 g |
| KCl | 0.20 g |
| $K_2HPO_4$ | 1.04 g |
| $KH_2PO_4$ | 0.32 g |

Methods

Measurement of the Concentration of Specific IgE in the s.c. Mouse Model by ELISA The relative concentrations of specific IgE serum antibodies in the mice produced in response to s.c. injection of proteins are measured by a three layer sandwich ELISA according to the following procedure:

1) The ELISA-plate was coated with 10 microgram rat anti-mouse IgE (Serotech MCA419; dilution 1:100) Buffer 1 (50 microL/well). Incubated over night at 4° C.
2) The plates were emptied and blocked with 2 (wt/v) % skim milk, PBS for at least ½ hour at room temperature (200 microL/well). Gently shaken. The plates were washed 3 times with 0.05 (v/v) % Tween20, PBS.
3) The plates were incubated with mouse sera (50 microL/well), starting from undiluted and continued with 2-fold dilutions. Some wells were kept free for buffer 4 only (blanks). Incubated for 30 minutes at room temperature. Gently shaken. The plates were washed 3 times in 0.05 (v/v) % Tween20, PBS.
4) The subtilase or subtilase variant was diluted in 0.05 (v/v) % Tween20, 0.5 (wt/v) % skim milk, PBS to the appropriate protein concentration. 50 microL/well was incubated for 30 minutes at room temperature. Gently shaken. The plates were washed 3 times in 0.05 (v/v) % Tween20, PBS.
5) The specific polyclonal anti-subtilase or anti-subtilase variant serum for detecting bound antibody was diluted in 0.05 (v/v) % Tween20, 0.5 (wt/v) % skim milk, PBS. 50 microl/well was incubated for 30 minutes at room temperature. Gently shaken. The plates were washed 3 times in 0.05 (v/v) % Tween20, PBS.
6) Horseradish Peroxidase-conjugated anti-pIg-antibody was diluted in 0.05 (v/v) % Tween20, 0.5 (wt/v) % skim milk, PBS. 50 microL/well was incubated at room temperature for 30 minutes. Gently shaken. The plates were washed 3 times in 0.05 (v/v) % Tween20, PBS.
7) 0.6 mg ODP/ml+0.4 microL $H_2O_2$/ml were mixed in Citrate buffer pH 5.2.
8) The solution was made just before use and incubated for 10 minutes.
9) 50 microL/well.
10) The reaction was stopped by adding 50 microL 2 N $H_2SO_4$/well.
11) The plates were read at 492 nm with 620 nm as reference.

Similar determination of IgG can be performed using anti mouse-IgG and standard rat IgG reagents.

Measurement of the Concentration of Specific IgE in the MINT Assay by ELISA

The relative concentrations of specific IgE serum antibodies in the mice produced in response to intranasal dosing of proteins are measured by a three layer sandwich ELISA according to the following procedure:

1) The ELISA-plate (Nunc Maxisorp) was coated with 100 microliter/well rat anti-mouse IgE Heavy chain (HD-212-85-IgE3 diluted 1:100 in 0.05 M Carbonate buffer pH 9.6). Incubated over night at 4° C.
2) The plates were emptied and blocked with 200 microliter/well 2% skim milk in 0.15 M PBS buffer pH 7.5 for 1 hour at 4° C. The plates were washed 3 times with 0.15 M PBS buffer with 0.05% Tween20.
3) The plates were incubated with dilutions of mouse sera (100 microL/well), starting from an 8-fold dilution and 2-fold dilutions hereof in 0.15 M PBS buffer with 0.5% skim milk and 0.05% Tween20. Appropriate dilutions of positive and negative control serum samples plus buffer controls were included. Incubated for 1 hour at room temperature. Gently shaken. The plates were washed 3 times in 0.15 M PBS buffer with 0.05% Tween20.
4) 100 microliter/well of subtilase or subtilase variant diluted to 1 microgram protein/ml in 0.15 M PBS buffer with 0.5% skim milk and 0.05% Tween20 was added to the plates. The plates were incubated for 1 hour at 4° C. The plates were washed 3 times with 0.15 M PBS buffer with 0.05% Tween20.
5) The specific polyclonal anti-subtilase or anti-subtilase variant serum for detecting bound antigen was diluted in 0.15 M PBS buffer with 0.15% skim milk and 0.05% Tween20. 100 microl/well was incubated for 1 hour at 4° C. The plates were washed 3 times in 0.15 M PBS buffer with 0.05% Tween20.
6) 100 microliter/well pig anti-rabbit Ig conjugated with peroxidase diluted 1:1000 in 0.15 M PBS buffer with 0.5% skim milk and 0.05% Tween20 was added to the plates. Incubated for 1 hour at 4° C. The plates were washed 3 times in 0.15 M PBS buffer with 0.05% Tween20.
7) 250 microliter/well 0.1 M Citrat/phosphat buffer pH 5.0 was added to the plates. Incubated for approximately 1 minute. The plates were emptied.
8) 100 microliter/well ortho-phenylenediamine (OPD) solution (10 mg OPD diluted in 12.5 ml Citrat/phosphat buffer pH 5.0 and 12.5 microliter 30% hydrogen peroxide added just before use) was added to the plates. Incubation for 4 minutes at room temperature.
9) The reaction was stopped by adding 150 microliter/well 1M $H_2SO_4$.
10) The plates were read at 490 nm with 620 nm as reference.

EXAMPLES

Example 1

Identification of Epitopes in Savinase

A high diversity library of phages expressing random oligomeric peptides (hexa, hepta, octa, nona and/or dodeca peptides) as part of their surface proteins, were screened for their capacity to bind antibodies. The phage libraries were obtained from Schafer-N, Copenhagen, Denmark and New England Biolabs Inc, UK.

Antibody samples were raised in animals (Rat, Rabbits or Mice) by parenteral or mucosal administration of each of the proteins listed below. The antibodies were dissolved in phosphate buffered saline (PBS). In some cases, antibodies of specific subclasses were purified from the serum of immunised animals by capryilic acid precipitation (for total IgG) or by affinity chromatography using paramagnetic immunobeads (Dynal AS) loaded with subtype-specific antibody (purification of IgG1, IgG4, IgE) or target protein, e.g. *Bacillus lentus* protease (Savinase™), for the isolation of target specific Rat IgG, Mouse IgG, Mouse IgE, and Rabbit IgG.

Protein-specific antibodies were also obtained from serum obtained from sensitised humans.

The phage libraries were incubated with antibody coated beads. E.g. phages expressing oligopeptides with affinity for mouse IgE antibodies captured rat anti-mouse IgE-coated beads, and were collected by exposing these paramagnetic beads to a magnetic field. The collected phages were eluted from the immobilised antibodies by mild acid treatment, by direct infection of phage-sensitive *E. coli* strains, by elution with intact protein antigen specific for the respective antibody sample (f.e. Savinase for anti-Savinase antibodies) or by a combination of these approaches. The isolated phages were amplified using methods known in the art.

The specific phage-clones were isolated from the cell supernatant by centrifugation in the presence of polyethylene glycol. DNA was isolated, the DNA sequence coding for the oligopeptide was amplified by PCR, and its DNA sequence was determined, all according to standard procedures known in the art. The amino acid sequence of the corresponding oligopeptide was deduced from the DNA sequence.

These experimentally determined reactive peptides were supplemented with information on reactive peptides published in the literature.

The sequences were collected in a database, and analysed by sequence alignment to identify epitope patterns.

Identifying Epitope Patterns

In principle, each of the reactive (oligo)peptide sequences represented an epitope pattern. However, some epitope patterns were redundant and to remove redundancy among the epitope patterns, the reactive (oligo)peptides sequences were subjected to computerised data analysis.

First all possible dipeptides were generated corresponding to $13^2$ different combinations taking conservative alternatives into account. The presence and frequency of each dipeptide among the reactive (oligo)peptide sequences were listed. Next all possible tripeptides were generated corresponding to $13^3$ different combinations and again the presence and frequency of each tripeptide among the reactive (oligo)peptide sequences were listed. All possible combinations of the listed dipeptides and tripeptides were then generated including those containing 1, 2, 3 or 4 residues inserted between the dipeptides and tripeptides, these residues selected among the possible residue types. This procedure generated a list of different peptide combinations of amino acids each containing at least one dipeptide and at lest one tripeptide from the initial listings as well as 0 to 4 residues in between. The frequency of each peptide combination among the reactive (oligo)peptide sequences were then ranked and relevant epitope patterns were selected by a procedure where reactive peptides covered by the most frequent combination were first selected and separated from the group of the reactive peptides. Then reactive peptides covered by the second most frequent combination were selected and separated from the remaining group. Then reactive peptides covered by the third most frequent combination were selected and separated from the remaining group. This procedure was repeated until combinations covering all reactive peptides are found.

Predicting Epitopes

The three-dimensional structure of SEQ ID NO:1 has been described in Betzel, C. et al.: "Crystal structure of the alkaline proteinase Savinase from *Bacillus lentus* at 1.4 A resolution" in Journal of Molecular Biology 223 pp. 427 (1992).

Surface accessibility was measured for each amino acid in SEQ ID NO:1 using the DSSP program (see W. Kabsch and C. Sander, Biopolymers 22 (1983) 2577-2637) in percent of a standard value for that amino acid. The standard values generated according to established methods by analysing average surface accessibility of an amino acid in a 20-mer homogeneous peptide in helix formation using the DSSP program. For each of the 13 different residue types (taking conservative alternatives into consideration) the average surface accessibility were as follows:

| Residue | Accessibility Å$^2$ |
|---|---|
| A | 62 |
| C | 92 |
| D | 69 |
| E | 156 |
| F | 123 |
| G | 50 |
| H | 130 |
| I | 84 |
| K | 174 |
| L | 97 |
| M | 103 |
| N | 85 |
| P | 67 |
| Q | 127 |
| R | 211 |
| S | 64 |
| T | 80 |
| V | 81 |
| W | 126 |
| Y | 104 |

Epitopes were predicted by a computer program on a 3-dimensional model of SEQ ID NO:1 by using the epitope patterns found as described above as follows:

(1) For all amino acids in SEQ ID NO:1 it was examined if (a) the amino acid type match the first amino acid of an epitope patterns and (b) the solvent surface accessibility greater than or equal to a predefined value, e.g., 20%. Those amino acid satisfying 1(a) and 1(b) are selected.

(2) For all amino acids within a distance of 10 Å from the amino acids selected in step 1 it is examined if (a) the amino acid type matches the second amino acid of the pattern and (b) the surface accessibility greater than or equal to the predefined value, e.g., 20%. Those amino acid satisfying 2(a) and 2(b) are selected (3) For all amino acids within a distance 10 Å from the amino acids selected in step 2 it is examined if (a) the amino acid type matches the third amino acid of the pattern and (b) the surface accessibility greater than or equal to the predefined value, e.g., 20%. Those amino acid satisfying 3(a) and 3(b) are selected.

(4) Repeating step 3 for all amino acids in the epitope pattern

Further, a limit of 25 Å was set as the maximum distance between any two epitope residues.

This procedure was carried out for all epitope patterns for each of the following settings for surface accessibility cut-off: 30, 40, 50, 60, 70 and 80%. Epitope patterns finding a match on the 3 dimensional structure of SEQ ID NO: 1 according this procedure is predicted as epitopes.

Finally, for each of the seven settings for solvent accessibility, a table of all amino acids of SEQ ID NO:1 was created, in which each amino acid residue was given a score by adding up the number of times it appeared in one of the epitopes (at that solvent setting). This score will be an indication of the likelihood that modification (substitution, insertion, deletion, glycosylation or chemical conjugation) of that amino acid will, result in a variant of lower antigenicity. All amino acids of the protein can then be ranked according to this score and those with highest scores can be selected for mutagenesis.

By studying the positions of the top 10% scoring amino acids in combination with topological mapping as described below on the three-dimensional model of SEQ ID NO:1, it is possible to identify relevant epitopes.

Topological Analysis of the Epitope Mapping Data

To get insight in the actual epitopes, coherent patches of amino acids were identified by visualising the mapping data on the relevant 3D-structure. Segments of ≧5 consecutive amino acids, the minimal length of each motif, were defined as the building blocks of the potential epitopes. For each of the identified segments, the neighbouring amino acids were determined using the SwissProt Pdb.viewer (www.ExPASy- .com). Neighbouring was defined empirically as being situated within 8 Å of any of the amino acids in the selected amino acid segment.

Applying the above described tools it has been possible to define 4 epitopes on the molecule. These are:

Epitope 1: P52-N62; A98-S105; G127-E136; Y167; R170.

Epitope 2: G127; P129; N155-S161; Y167; R170; S188; Y192-G195; N218; N261-L262.

Epitope 3: A1-W6; P14-N18; T38-I44; Q59-N62; L75-I79; S87; N155; N204-N218.

Epitope 4: N6; Q12; G157-S161; D181-N185; Y192-G195; T255-S265.

Example 2

Library Construction

Applying the procedure outlined in Example 1 above, the subtilase variants may be obtained by mutagenesis of the corresponding nucleic acid sequences as described in for example Sambrook et al. (1989), Molecular Cloning. A Laboratory Manual, Cold Spring Harbour, N.Y.).

Example 3

Cloning and Expression of Subtilase Variants

Variants of the invention comprising specific insertions/deletions/substitutions are made by traditional cloning of DNA fragments (Sambrook et al., Molecular Cloning: A Laboratory Manual, 2nd Ed., Cold Spring Harbor, 1989) produced by PCR with oligos containing the desired mutations.

The template plasmid DNA may be pSX222, or an analogue of this containing a variant of the enzyme in SEQ ID NO 1. Mutations are introduced by oligo directed mutagenesis to the construction of variants.

The variants are transformed into *E. coli*. DNA purified from an over night culture of these transformants is transformed into *B. subtilis* by restriction endonuclease digestion, purification of DNA fragments, ligation, transformation of *B. subtilis*. Transformation of *B. subtilis* is performed as described by Dubnau et al., 1971, J. Mol. Biol. 56, pp. 209-221.

Site-Directed Mutagenesis in Order to Introduce Mutations in a Specific Region:

The overall strategy used to perform site-directed mutagenesis is:

Mutagenic primers (oligonucleotides) are synthesized corresponding to the DNA sequence flanking the sites of mutation, separated by the DNA base pairs defining the insertions/deletions/substitutions.

Subsequently, the resulting mutagenic primers are used in a PCR reaction with the modified plasmid pSX222. The resulting PCR fragment is purified and extended in a second PCR-reaction, the resulting PCR product is purified and extended in a third PCR-reaction before being digested by endonucleases and cloned into the *E. coli-B. subtilis* shuttle vector pSX222. The PCR reactions are performed under normal conditions. The plasmid DNA is transformed into *E. coli* by well-known techniques and one *E. coli* colony is sequenced to confirm the mutation designed.

Fermentation

Fermentations for the production of subtilase enzymes were performed at 37° C. on a rotary shaking table (300 r.p.m.) in 500 ml baffled Erlenmeyer flasks containing 100 ml BPX medium for 5 days.

Consequently, in order to make e.g. a 2 litre broth 20 Erlenmeyer flasks were fermented simultaneously.

Media:

| BPX Medium Composition (per liter) | |
|---|---|
| Potato starch | 100 g |
| Ground barley | 50 g |
| Soybean flour | 20 g |
| Na2HPO4 × 12H2O | 9 g |
| Pluronic | 0.1 g |
| Sodium caseinate | 10 g |

The starch in the medium was liquefied with α-amylase and the medium was sterilized by heating at 120° C. for 45 minutes. After sterilization the pH of the medium was adjusted to 9 by addition of NaHCO3 to 0.1 M.

Example 4

Purification of Subtilase Variants

This procedure relates to purification of 2 litre scale fermentation for the production of the subtilases of the invention in a *Bacillus* host cell.

Approximately 1.6 litres of fermentation broth was centrifuged at 5000 rpm for 35 minutes in 1 litre beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered at room temperature prior to absorption on a Bacitracin affinity column at pH 7. The subtilase was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm diameter) equilibrated with a buffer containing 0.01 dimethylglutaric acid, 0.2 M boric acid and 0.002 m calcium chloride adjusted to pH 6.5.

By using the techniques mentioned above for the construction and fermentation, and the above isolation procedure, the novel subtilase of the present invention was produced and isolated.

This procedure was applied when purifying the subtilases of the present invention listed in table 1.

The procedure described in WO 03/037914 (Novozymes A/S) was applied when purifying the subtilases of the present invention listed in table 2.

Example 5

Competitive ELISA

Immunoplates (Nunc Maxisorb; Nunc) are coated overnight at 4° C. with a suitable dose, or dose-range, of wild type allergen. The plates are then washed thoroughly with Phosphate Buffered Saline (PBS) containing 0.05% Tween 20 (PBST), and remaining binding sites are blocked with PBS containing 2% Skim Milk Powder (SMP). Dilute in a dose-range the recombinant competitor protease polypeptide variant in PBS containing 0.5% SMP, 0.05% Tween 20 and mix with antigen specific rabbit polyclonal antibody diluted typically 2000-10,000 times in the same buffer. Add the mixture to each well and incubated 2 h at 20° C. under gentle agitation.

Following a thorough wash with PBST, the allergen-IgG complexes are detected, by serial incubation with an anti-rabbit antibody (DAKO), and goat anti-rabbit Ig coupled to horse-radish peroxidase. The enzymatic activity is measured by adding TMB Plus (Kem-En-Tec) as substrate, and stopping the reaction with an equal volume of 0.2 M $H_2SO_4$, and detecting colour development by measuring optical density at 450 nm (OD450) in an ELISA plate reader. If antigen specific rabbit polyclonal antibody binds to the protease polypeptide variant in solution, it will reduce binding to the plate-bound wild type polypeptide, thus reducing the OD450.

The above procedure was applied on large number of variants. Selection of interesting protease variants by competitive ELISA was based upon:

1. Residual binding (%) of antibody after competition with increasing amounts of variant as compared to the plate bound protein of SEQ ID NO: 1 with the insertion *99aE, and
2. Shift of the IC50% (IC: Inhibiting concentration) to higher or lower concentrations as reflecting differences in binding affinity.

Variants were evaluated upon either purification or micro-purification.

Residual binding (%) is the ratio between OD450 measured at the highest competitor concentration and OD450 measured in the absence of competitor. The residual binding with the parent protein as competitor is typically 0%. Variants typically move in terms of residual binding towards 100%.

Differences in binding affinity are expressed as an X-fold increase or decrease of the amount of variant required obtaining a 50% inhibition of antibody binding to the parent protein, as compared to the parent protein itself. The inventors surprisingly observed that higher affinity of the variant for anti-parent protein specific antibody correlated as well very well with a decrease in allergenic potential in animals. Differences in binding affinity can not be determined for variants revealing a >50% residual binding.

Competitive ELISA of Purified Protease Variants

TABLE 1

Evaluation of purified protease variants

| Variant no. | Mutations | Wash performance at 5 nM | Residual binding | Binding affinity |
|---|---|---|---|---|
| 1P | S57P, *99aE, R247Q | >REF. | 11% | 7.5x |
| 2P | *99aE, A158V | >REF. | 0% | 0.6x |
| 3P | *99aE, E136G | >REF. | n.d. | n.d. |
| 4P | *99aE, E136K | <REF. | n.d. | n.d. |
| 5P | I79T, *99aE, Q191E | >REF. | 13% | 4x |
| 6P | *99aE, S141N, S156D | >REF. | 0% | 2x |
| 7P | T58A, *99aE, S156N | as REF. | 0% | 1.5x |
| 8P | *99aE, S141G, S156N, Q191E | as REF. | 0% | 3x |
| 9P | S78P, *99aE, N185S, Q206L | >REF. | 19% | 17x |
| 10P | *99aE, G195P, T260L | >REF. | 35% | n.m |
| 11P | *99aE, G160S, G211S, T260N | >REF. | 0% | 2.6x |
| 12P | *99aE, G195D, G211N, T260L | >REF. | 66% | n.m |
| 13P | *99aE, G160S, G195P, G211S, T260N | >REF. | 57% | n.m |
| 14P | *99aE, A158N, S161D | >REF. | 4% | 2.3x |
| 15P | *99aE, S259N, T260I | >REF. | 0% | 1.2x |
| 16P | *99aE, S259N | >REF. | 0% | 1.2x |
| 17P | *99aE, S259R | as REF. | 0% | 1.0x |
| 18P | T22A, *99aE, G160N, T260L | >REF. | 0% | 2.9x |
| 19P | *99aE, G160D, G195P, G211P, T260N | >REF. | 21% | 31x |
| 20P | *99aE, G160S, G211D, T260L | >REF. | 0% | 1.5x |

Explanation of abbreviations used in table 1 above:
n.m.: not measurable;
n.d.: not determined.
">REF." indicates that wash performance is better than reference enzyme.
"<REF." indicates that wash performance is poorer than reference enzyme.
"as REF." indicates that wash performance is as reference enzyme.
The reference enzyme is the enzyme disclosed in SEQ ID NO 1 with the insertion *99aE.

All the above candidates have subsequently been evaluated with respect to wash performance according to the procedure described in Example 6.

Results of the wash performance evaluation are shown in table 1.

Competitive ELISA of Micro-Purified Protease Variants

A number of variants were micro-purified; upon micro-purification residual binding and binding affinity was evaluated.

TABLE 2

Evaluation of micro-purified protease variants

| id no | Mutations | Residual binding | Binding affinity |
|---|---|---|---|
| 922.03 | S9G, *99aE, A158N, G160D, S161D, N184S | n.m | n.m. |
| 922.06 | P52S, *99aE, A158D, S161G | 0% | 0.6x |
| 923.06 | *99aE, T260P | 0% | 1.7x |
| 923.14 | *99aE, T260I | 0% | 0.6x |

TABLE 2-continued

Evaluation of micro-purified protease variants

| id no | Mutations | Residual binding | Binding affinity |
|---|---|---|---|
| 923.16 | *99aE, S259P | 0% | 0.4x |
| 924.16 | *99aE, G160S, S163T, G195S, G211S, K237R, G258A, T260L | n.m | n.m. |
| 924.20 | G23S, *99aE, G160N, G195D, V203G | n.m | n.m. |
| 923.23 | *99aE, G160P, G195P, V205A, G211P, T260N | n.m | n.m. |
| 924.24 | V95A, *99aE, G211N, T260L | n.m | n.m. |
| 924.25 | T66S, *99aE, G160N, G195N, G211P, T260I | n.m | n.m. |
| 924.26 | *99aE, G160S, G195P, G211P, T260L | n.m | n.m. |
| 924.29 | L82P, *99aE, I107T, G160N, Q182R, G211D, K251R, T260I | n.m | n.m. |
| 926.04 | Y91H, *99aE | 0% | 0.3x |
| 926.14 | Q12R, *99aE, S156H | 0% | 0.5x |
| 926.29 | *99aE, S156H, K251E | n.m | n.m. |
| 923.07 | *99aE, T260N | 0% | 2.6x |
| 923.10 | *99aE, T260D | 0% | 1.6x |
| 924.13 | *99aE, G195N, G211P, T260I | n.m | n.m. |
| 924.14 | *99aE, G160S, A172S, N204T, G211P, T260N | n.m | n.m. |
| 924.15 | *99aE, G160S, G211P, T260L | n.m | n.m. |
| 924.17 | *99aE, M175I, G195S, T260L | n.m | n.m. |
| 924.18 | W6L, *99aE, G160S, G195N, S256N, T260L | n.m | n.m. |
| 925.1 | *99aE, Y192M, M222V, L262Q | 0% | 0.1x |
| 925.2 | *99aE, Y192W, L262Q | 0% | 0.1x |
| 926.27 | *99aE, S156H, Q191E | 0% | 1.1x |
| 926.28 | N77D, *99aE, S156N, Q191N | 0% | 1.2x |
| 926.30 | *99aE, S141G, S156D, M175I | 0% | 1.8x |
| 926.31 | *99aE, Q191N | 0% | 0.9x |
| 926.32 | *99aE, S156D | 0% | 0.6x |
| 926.33 | *99aE, S156N, Q191N, Y263H | 0% | 0.8x |

n.m.: not measurable

Example 6

Test of the Wash Performance of Variants

Wash conditions: Temperature 30° C., wash time 14 min, water hardness 6° dH, detergent concentration 1.5 g/l with enzyme concentration 5, 10 and 30 nM. As benchmarking enzyme the enzyme of SEQ ID NO 1 with the insertion *99aE was used.

The detergents were commercial detergents which were inactivated by making a detergent solution and heat it for 5 min. at 85° C. in the microwave oven.

pH was "as is" in the current detergent solution and was not adjusted.

Water hardness was adjusted by adding CaCl2*2H2O; $MgCl_2*6H_2O$; $NaHCO_3$ ($Ca^{2+}$:$Mg^{2+}$:$HCO_3^-$=2:1:6) to milli-Q water.

The test material was polyester/cotton swatches soiled with blood/milk/carbon black (EMPA 117, available from EMPA testmaterials, Mövenstrasse 12, CH-9015 St. Gallen).

After wash the reflectance (R) of the test material was measured at 460 nm using a J&M Tidas MMS spectrophotometer. The measurements were done according to the manufacturers' protocol.

$R_{Variant}$: Reflectance of test material washed with variant $R_{Blank}$: Reflectance of test material washed with no enzyme delta-Reflectance Rvariant−Rblank The higher the delta-Reflectance the better is the wash performance. The delta-Reflectance was calculated for the dosage 5 nM enzyme.

Example 7

Epithelial Cell Assay

Reduced allergenicity was verified in vitro by stimulation of human airlifted epithelial cells with enzyme variants. The presence of M-CSF, secreted into the culture medium in the well in response to enzyme exposure was measured by sandwich ELISA. The dose response curve of the M-CSF response to enzyme variants and reference protein was compared (see table 3). Variants with reduced allergenicity and adjuvancy were found to require higher doses in order to elicit comparable cytokine responses.

Reference protein for this study was the enzyme of SEQ ID NO 1 with a *99aE insertion.

Figure 3:
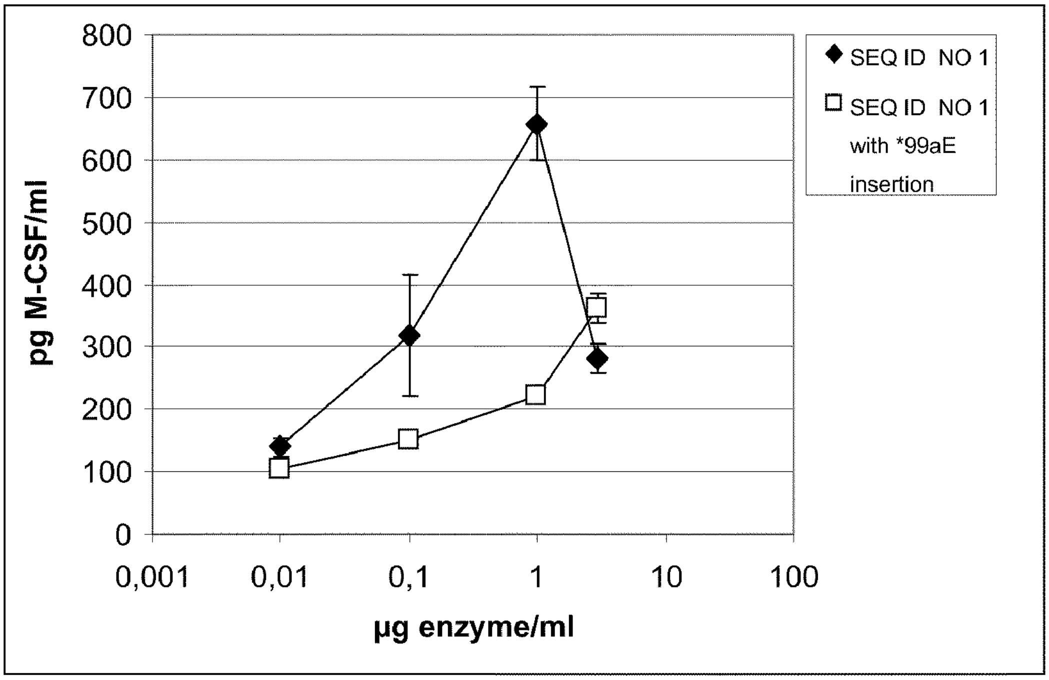
FIG. 3 shows a M-CSF-enzyme dose/response curve for human epithelial cell cultures exposed to the enzymes of SEQ ID NO1 and SEQ ID NO1 with a *99aE insertion.

FIG. 3 shows a response curve for the enzymes of SEQ ID NO1 and SEQ ID NO1 with a *99aE insertion. The figure clearly indicates that a protein showing reduced M-CSF production as compared to the reference enzyme of the present example will also show a reduced M-CSF production when compared with the enzyme of SEQ ID NO 1.

Cell Culture Reagents

Epithelial Cells and Cell Growth Medium:

The human type-II alveolar cell line, A549 derived from human lung carcinoma, was purchased from American Type Culture Collection (ATCC). A549 cells were cultured in Dulbecco's MEM/NUT mix F12 (DMEM/F12) medium with L-Glutamine, 15 MM HEPES, 10.000 IE Penicillin/10.000 µg/ml Streptomycin (GIBCO Invitrogen) supplemented with 0.5% Ultroser G (BioSepra). This medium is referred to as cell culture medium.

A549 cells were cultured in tissue culture flasks in cell culture medium (37° C., 5% CO2 and 100% humidity). Before cells were added, tissue culture flasks were coated with 2% Ultroser G at room temperature. After 10 min. incubation, Ultroser G was removed and cells in cell culture medium were plated into flasks and incubated for 7-10 days. Medium was changed every second day. When cells reached 70-80% confluence in monolayers, they were passaged into a new 2% Ultroser G-coated tissue culture flask. Cell culture medium was removed from the tissue culture flask and the adherent A549 cells were rinsed with Hank's Balanced Salts (HBSS) w/o Calcium and Magnesium (GIBCO). HBSS was removed and 1× Trypsin-EDTA solution was added and incubated for 10 min. (or until the cells detach) at 37° C. Fresh cell culture medium was added, aspirated and medium with detached cells were dispensed into either a new 2% Ultroser G-coated tissue flask or seeded on 1% Ultroser G-coated 0.4 μm Polycarbonate membranes (inserts) (Nunc) in an airlifted human cell stimulation assay. Cell viability was analysed by trypan blue staining and was found to be between 75-95%. Cells were used between passages 80-95.

Human Airlifted Epithelial Cell Cultures 25 mm polycarbonate tissue culture inserts were placed in wells on a tissue culture plate. The polycarbonate tissue culture inserts were coated with 1% Ultroser G for 10 min. at room temperature. After 10 min. incubation, Ultroser G was removed. 1.5 ml of $1.33 \times 10^5$ cells/ml in cell culture medium was seeded on the polycarbonate tissue culture insert and 1.5 ml cell culture medium was added in the well. Cells were cultured for 10 days in the insert with fresh cell culture medium added every second day in the insert and the well. On day 7 the cells were airlifted and a liquid-air interface was created. This was done by removal of medium from the inserts and the well. Fresh cell culture medium was then added to the well and the airlifted cell cultures were grown for 3 days more. On day 10, fresh cell culture medium was added to the well and 150 μl of cell culture medium with increasing concentrations of enzyme was added to the insert (on top of the cells). After 4 hours enzyme incubation, the cell culture medium in the well (under the cells) was harvested and stored at −20° C. until analysis with cytokine ELISA. After removal of cell culture medium, cell viability was measured using AlamarBlue assay (SeroTec). The polycarbonate insert was cut of into the well and 1 ml of fresh cell culture medium in addition to 125 μl AlamarBlue was added to each well and incubated for 4 hours at 37° C. with 5% CO2. AlarmarBlue reduction was then measured fluorometrically and cell viability was calculated for each dose of each enzyme variant tested (% viability=(signal with enzymes/signal with medium alone)*100%). Viability on 90-110% was found acceptable.

Cytokine ELISA

The presence of the cytokine M-CSF secreted into the cell culture medium in response to enzyme exposure was measured using a sandwich ELISA.

The following data were obtained using the cell epithelial assay on selected variants:

TABLE 3

M-CSF secretion of human airlifted epithelial cell cultures in response to enzyme variant stimulation

| Variant | [μg/ml enzyme variant to stimulate 300 pg/ml M-CSF production] relative to [μg/ml reference enzyme[a] to stimulate 300 pg/ml M-CSF production] |
|---|---|
| SEQ ID NO 1 with *99aE insertion | 1[a] |
| 5P | 2.2 |
| 6P | 1.2 |
| 10P | 2.5 |
| 11P | 1.3 |
| 13P | 1.2 |
| 18P | 1.1 |
| 19P | 1.5 |

[a]M-CSF production in response to enzyme stimulation in separated experiments was normalized with reference protein. The reference protein in this Example is SEQ ID NO 1 with *99aE insertion.

The data disclosed in table 3 shows that the two variants 5P and 10P have a reduced allergenicity profile as compared to the reference enzyme.

Example 8

Testing of SEQ ID NO 1 Variants for Reduced Allergenicity in Vivo (MINT Assay)

Mouse intranasal (MINT) model (Robinson et al., Fund. Appl. Toxicol. 34, pp. 15-24, 1996).

Mice were dosed intranasally with the proteins on the first and third day of the experiment and from thereon on a weekly basis for a period of 5 weeks. Blood samples were taken 15, 31 and 45 days after the start of the dosing. Serum was subsequently analysed for IgG1 (day 15) or IgE (day 31 and 45) levels.

The variants 5P (I79T+*99aE+Q191E) and 10P (*99aE+G195P+T260L) (both inactive) were compared to SEQ ID NO 1 (in 0.9% NaCl).

The mean titres are shown in FIG. 1:

The IgG1 and IgE titres are expressed as the reciprocal of the highest dilution giving a positive ELISA reading converted to log 2. A reading is regarded as positive if higher than the OD-mean+2× standard deviation of the negative controls. There were 6 mice per dose level and the results are expressed as group mean titres.

From FIG. 1 it can be concluded that the variants 5P (I79T+*99aE+Q191E) and 10P (*99aE+G195P+T260L) have considerably less potential for eliciting the production of antigen specific IgG1 and IgE antibody than those of the benchmark proteins, SEQ ID NO 1.

Example 9

Test of Performance of Subtilase Variants in Automatic Dishwashing (ADW)

The performance of the subtilase of the invention in full scale ADW is tested in a household dish wash composition using standard conditions. The soil used is an egg/milk mixture coated on a steel plate. Further, a ballast soil containing various foodstuffs is added.

Example:

Detergent: Commercial or model detergent.

Detergent dosage 5.0 g/l pH As is.

Water hardness: 3° dH to 21° dH

Temperature: 45° C. to 65° C.

Enzyme concentration: 10 nM to 230 nM, based on the total volume of wash water in the machine.

Test method: Egg/milk or egg yolk soiling on steel plates as described below.

Machine: Bosch or other commercially available.

Wash Program:

Tap water is used; the following steps are applied:

| Step | Time (seconds) | Temperature |
|---|---|---|
| Main wash | 1200[1)] | 50° C.[2)] |
| Rinse | 300[1)] | 39° C.[2)] |
| Dry | 1530 | 65° C. |

[1)]Heating of tap water takes place during the indicated time interval.
[2)]Final temperature upon heating of tap water.

Egg/Milk Soiling for Full Scale ADW Test

Materials:

220 ml full cream milk 15 eggs, medium size

Steel plates, diameter 18 cm

The dish wash composition is heated at 85° C. for 5 minutes in a microwave oven in order to inactivate enzyme activity in the composition.

Soiling of Steel Plates:

220 ml full cream milk is mixed with 15 raw eggs in a Braun UK 20 kitchen machine for 2 minutes. After sieving, stainless steel plates are soiled in the mixture by immersion.

The plates are dried overnight at room temperature in an upright position. The dried plates are then heated at 120° C. for 45 minutes in order to denature the proteins on the surface.

Egg Yolk Soiling for Full Scale ADW Test

Materials:

3 dL pasteurized egg yolk.

Steel plates, diameter 18 cm

The dish wash composition is heated at 85° C. for 5 minutes in a microwave oven in order to inactivate enzyme activity in the composition.

Soiling of Steel Plates:

The steel plates are weighed on a balance giving 3 decimals.

Approx. 3 dL pasteurized egg yolk is mixed thoroughly and sieved through a kitchen screen.

The egg yolk broth is rolled onto the plates in a thin layer, e.g. using a paint roller. This is done twice (without drying in between and with the roller dipped in egg yolk also the second time).

The resulting layer of egg yolk should be around 1 g.

The plates are left to dry for minimum 4 hours at room temperature.

The soiled plates and the racks are then lowered into boiling demineralised water for precisely 30 seconds.

The plates are left to dry for 30 minutes at room temperature.

After drying at room temperature the plates are dried in an oven at 80° C. for 30 minutes.

The plates are left to cool at room temperature for 30-60 minutes after which they are weighed again.

Upon washing and drying at room temperature the plates are dried in the oven at 80° C. for 30 min.

Again after cooling at room temperature for 30-60 minutes the plates are weighed.

ADW Experiments

For each experiment, 10 soiled plates are washed in accordance with conditions listed above. In addition to the soiled plates, the machine is filled up with 10 porcelain plates, 4 glasses, 4 cups and 16 pieces of cutlery.

Furthermore, 50 g of ballast slurry is added to the machine. The composition of the slurry is as follows:

3000 g are made, and the following components are weighed out:

| Step | Materials | Dosage (g) |
|---|---|---|
| 1 | Margarine | 189 |
| | Lard | 189 |
| | Deep-Fry Oil | 189 |
| | Gravy Powder | 51 |
| 2 | Rapeseed Oil | 948 |
| | Egg | 474 |
| 3 | Ketchup | 189 |
| | Mustard | 189 |
| 4 | Double Cream, 38% fat | 282 |
| | Full-Cream Milk, 3.5% fat | 189 |
| 5 | Potato Flour | 66 |
| | Wheat Flour | 18 |
| | Quark powder | 18 |
| | Benzoic Acid | 9 |

1. Margarine, lard and deep-fry oil are melted at low temperature. Afterwards sieved gravy powder is added—under good stirring—and is cooled down to 40° C.
2. Rapeseed oil and egg are mixed.
3. Ketchup and mustard are added into the oil/egg mass followed by 5 minutes mixing.
4. The under 1) produced fat/gravy (cooled) is slowly added to the mixture produced in 3) and mixed for further 5 minutes.
5. Double cream and full-cream milk are added the mixture and mixed for 5 minutes.
6. The last flours and powders (step 5 in the table) is added. The ballast slurry is mixed to a smooth mass.
7. The Ballast slurry is weighed out in portions of 50 g.

Measurements and Calculations for Egg/Milk

The light reflection values (R-values) are measured at six different locations on the plates using a Minolta Chroma Meter (Type: CR-300). Measurements are made on clean plates ($R_{clean}$), on soiled plates after heating ($R_{soiled}$) and on plates after wash ($R_{after\ wash}$).

The removed protein film (% RPF) is calculated according to the below formula:

$$\%\ RPF=100\%\times(R_{after\ wash}-R_{soiled})/(R_{clean}-R_{soiled})$$

Measurements and Calculations for Egg Yolk

Performance data originate from gravimetric measurements of the steel plates as clean, soiled and washed. The performance is calculated as:

$$\%\ \text{Removed Protein Film}\ (\%\ RPF) = \frac{(Weight_{soiled} - Weight_{washed})\times 100}{Weight_{soiled} - Weight_{clean}}$$

Data Analysis

% RPF is fitted as a function of mg enzyme protein added.

The data are fitted by means of a four-parameter logistic model that can be written as:

$$F(z)=Y_0+V_{max}*C^{\lambda}/(k_s^{\lambda}+C^{\lambda})$$

Where F(z) is the response calculated from $Y_0$ as the intercept, $Y_0+V_{max}$ being maximum response, C the enzyme dosage and $k_s$ being the half-saturation value. λ is the steepness parameter that in a Michaelis-Menten model is equal 1, but here it is equal or different from one as we are allowing S-shaped curves to be fitted.

Each curve fit is compared to the performance of the reference enzyme.

The invention claimed is:

1. A variant of the parent subtilase of SEQ ID NO:1 having reduced immunogenicity when compared to a variant with a single insertion of glutamic acid after position 99 as determined by ELISA measurement of cytokine M-CSF production after exposure of a human type-II alveolar epithelial cell line, said variant consisting of the amino acid sequence modifications I79T+*99aE+Q191E, wherein the positions for modification are numbered according to the amino acid sequence of subtilisin BPN' as set forth in SEQ ID NO:5 herein.

2. A composition comprising the variant according to claim 1 and a surfactant.

3. An isolated DNA sequence encoding the variant of claim 1.

4. A vector comprising the DNA sequence of claim 3.

5. An isolated host cell comprising the vector of claim 4.

* * * * *

SEQUENCE LISTING

```
<160> NUMBER OF SEQ ID NOS: 5

<210> SEQ ID NO 1
<211> LENGTH: 269
<212> TYPE: PRT
<213> ORGANISM: Bacillus lentus
```

<220> FEATURE:
<221> NAME/KEY: mat_peptide
<222> LOCATION: (1)..(269)

<400> SEQUENCE: 1

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 2
<211> LENGTH: 7
<212> TYPE: PRT
<213> ORGANISM: Artificial sequence
<220> FEATURE:
<223> OTHER INFORMATION: Synthetic construct

<400> SEQUENCE: 2

```
Ala Lys Ser Asn Asn Lys Arg
1               5
```

<210> SEQ ID NO 3
<211> LENGTH: 7
<212> TYPE: PRT
<213> ORGANISM: Artificial sequence
<220> FEATURE:
<223> OTHER INFORMATION: Synthetic construct

<400> SEQUENCE: 3

-continued

Ala Lys Ser Met Asn Lys Arg
1 5

<210> SEQ ID NO 4
<211> LENGTH: 7
<212> TYPE: PRT
<213> ORGANISM: Artificial sequence
<220> FEATURE:
<223> OTHER INFORMATION: Synthetic construct

<400> SEQUENCE: 4

Ala Lys Thr Pro Asn Lys Lys
1 5

<210> SEQ ID NO 5
<211> LENGTH: 275
<212> TYPE: PRT
<213> ORGANISM: Bacillus

<400> SEQUENCE: 5

Ala Gln Ser Val Pro Tyr Gly Val Ser Gln Ile Lys Ala Pro Ala Leu
1 5 10 15

His Ser Gln Gly Tyr Thr Gly Ser Asn Val Lys Val Ala Val Ile Asp
20 25 30

Ser Gly Ile Asp Ser Ser His Pro Asp Leu Lys Val Ala Gly Gly Ala
35 40 45

Ser Met Val Pro Ser Glu Thr Asn Pro Phe Gln Asp Asn Asn Ser His
50 55 60

Gly Thr His Val Ala Gly Thr Val Ala Ala Leu Asn Asn Ser Ile Gly
65 70 75 80

Val Leu Gly Val Ala Pro Ser Ala Ser Leu Tyr Ala Val Lys Val Leu
85 90 95

Gly Ala Asp Gly Ser Gly Gln Tyr Ser Trp Ile Ile Asn Gly Ile Glu
100 105 110

Trp Ala Ile Ala Asn Asn Met Asp Val Ile Asn Met Ser Leu Gly Gly
115 120 125

Pro Ser Gly Ser Ala Ala Leu Lys Ala Ala Val Asp Lys Ala Val Ala
130 135 140

Ser Gly Val Val Val Val Ala Ala Ala Gly Asn Glu Gly Thr Ser Gly
145 150 155 160

Ser Ser Ser Thr Val Gly Tyr Pro Gly Lys Tyr Pro Ser Val Ile Ala
165 170 175

Val Gly Ala Val Asp Ser Ser Asn Gln Arg Ala Ser Phe Ser Ser Val
180 185 190

Gly Pro Glu Leu Asp Val Met Ala Pro Gly Val Ser Ile Gln Ser Thr
195 200 205

Leu Pro Gly Asn Lys Tyr Gly Ala Tyr Asn Gly Thr Ser Met Ala Ser
210 215 220

Pro His Val Ala Gly Ala Ala Ala Leu Ile Leu Ser Lys His Pro Asn
225 230 235 240

Trp Thr Asn Thr Gln Val Arg Ser Ser Leu Glu Asn Thr Thr Thr Lys
245 250 255

Leu Gly Asp Ser Phe Tyr Tyr Gly Lys Gly Leu Ile Asn Val Gln Ala
260 265 270

Ala Ala Gln
275